(12) United States Patent
Fischer et al.

(10) Patent No.: US 7,385,051 B2
(45) Date of Patent: Jun. 10, 2008

(54) FLUORESCENT $N^2$,N3-ETHENO-PURINE (2'-DEOXY) RIBOSIDE DERIVATIVES AND USES THEREOF

(75) Inventors: Bilha Fischer, Shoham (IL); Einat Sharon, Rishon LeZion (IL)

(73) Assignee: Bar-Ilan University, Ramat Gan (IL)

( * ) Notice: Subject to any disclaimer, the term of this patent is extended or adjusted under 35 U.S.C. 154(b) by 312 days.

(21) Appl. No.: 11/337,438

(22) Filed: Jan. 24, 2006

(65) Prior Publication Data

US 2006/0166248 A1     Jul. 27, 2006

Related U.S. Application Data

(60) Provisional application No. 60/645,591, filed on Jan. 24, 2005.

(51) Int. Cl.
  *C07H 21/00*  (2006.01)
  *C07H 15/24*  (2006.01)
(52) U.S. Cl. ................. 536/25.32; 536/18.7; 536/22.1; 536/24.2
(58) Field of Classification Search ............... None
  See application file for complete search history.

(56) References Cited

OTHER PUBLICATIONS

Jerzy Boryski, "1,$N^2$-Ethenoguanosine: Three Methods of Synthesis", *Nucleosides & Nucleotides*, vol. 9(6), pp. 803-813, 1990.
Patrik R. Callis, "Electronic States And Luminescence Of Nucleic Acid Systems", *Annual Reviews Phys. Chem.*, vol. 34, pp. 329-357, 1983.
Jack J. Fox et al., "Thiation of Nucleosides. I. Synthesis of 2-Amino-6-mercapto-9-β-D-ribofuranosylpurine ("Thioguanosine") and Related Purine Nucleosides", *J. Am. Chem. Soc.*, vol. 80, pp. 1669-1675, 1958.
Rajesh Khazanchi et al., "$N^2$, 3-Etheno-2'-deoxyguanosine [8,9Dihydro-9-oxo-2'-deoxy-3-β-D-ribofuranosylimidazo[2,1-b]purine]: A Practical Synthesis and Characterization", *J. Org. Chem.*, vol. 58, pp. 2552-2556, 1993.
Pei-Pei Kung et al., "One-Flask Syntheses of 6-Thioguanosine and 2'-Deoxy-6- Thioguanosine", *Tetrahedron Lett.*, vol. 32, pp. 3919-3922, 1991.
J. T. Kusmierek et al., "Synthesis and Properties of $N^2$,3-Ethenoguanosine and $N^2$,3- Ethenoguanosine 5'-Diphosphate", *J. Org. Chem.*, vol. 52, pp. 2374-2378, 1987.
J. T. Kusmierek et al., "1,N2-Ethenodeoxyguanosine: Properties and Formation in Choloroacetaldehyde-Treated Polynucleotides and DNA", *Chem. Res. Toxicol.*, vol. 5, pp. 634-638, 1992.
E. A. Veliz et al., "C6 substitution of inosine using hexamethylphosphorous triamide in conjunction with carbon tetrahalide or N-halosuccinimide", *Tetrahedron Letters*, vol. 21, pp. 1695-1697, 2000.
Nelson J. Leonard, "Etheno-Bridged Nucleotides in Structural Diagnosis and Carcinogenesis", *Biochem. Mol. Biol.*, vol. 3, pp. 273-297, 1992.
Nelson J. Leonard, "Etheno-Substituted Nucleotides and Coenzymes: Fluorescence and Biological Activity", *CRC Crit. Rev. Biochem.*, vol. 15, pp. 125-185, 1984.
P. D. Sattsangi et al., "1,$N^2$-Ethenoguanine and $N^2$,3-Ethenoguanine. Synthesis and Comparison of the Electronic Spectral Properties of These Linear and Angular Triheterocycles Related to the Y Bases", *J. Org. Chem.*, vol. 42, No. 20, pp. 3292-3296, 1977.
J. A. Secrist III et al., "Fluoerescent Modification of Adenosine-Containing Coenzymes. Biological Activities and Spectroscopic Properties", *Biochemistry*, vol. 11, No. 19, Sep. 12, 1972.
J. A. Secrist III et al., "Synthesis and Biologic Evaluation of 8-substituted Derivatives of Nebularine (9-β-D-Ribofuranosylpurine)", *Nucleosides & Nucleotides*, vol. 13, No. 5, pp. 1017-1029, 1994.
R. W. Thomas et al., "Examples Of The Use Of Fluorescent Heterocycles In Chemistry And Biology", *Heterocycles*, vol. 5, pp. 839-882, 1976.
C. Vohringer et al., "A chimeric Rat Brain $P2Y_1$ Receptor Tagged with Green-fluorescent Protein: High-affinity Ligand Recognition of Adenosine Diphosphates and Triphosphates and Selectivity Identical to That of the Wild-type Receptor", *Biochem. Pharmacol.*, vol. 59, pp. 791-800, 2000.
Gregor Zundorf et al., "Novel modified adenosine 5'-triphosphate analogues pharmacologically characterized in human embryonic kidney 293 cells highly expressing rat brain $P2Y_1$ receptor: biotinylated analogue potentially suitable for specific $P2Y_1$ receptor isolation", *Biochem. Pharmacol.*, vol. 61, pp. 1259-1269, 2001.

*Primary Examiner*—Patrick Lewis
(74) *Attorney, Agent, or Firm*—Browdy and Neimark

(57) ABSTRACT

The invention relates to fluorescent $N^2$,N3-etheno-purine (2'-deoxy) riboside derivatives and fluorescent oligonucleotide probes comprising one or more moieties thereof, their preparation and uses thereof for staining DNA/RNA and for detection and quantitation of genetic material.

17 Claims, 4 Drawing Sheets

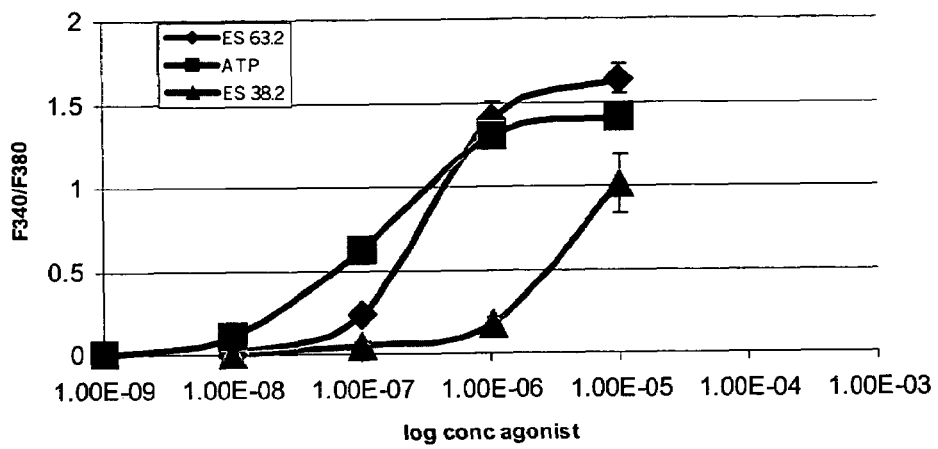
Fig. 6
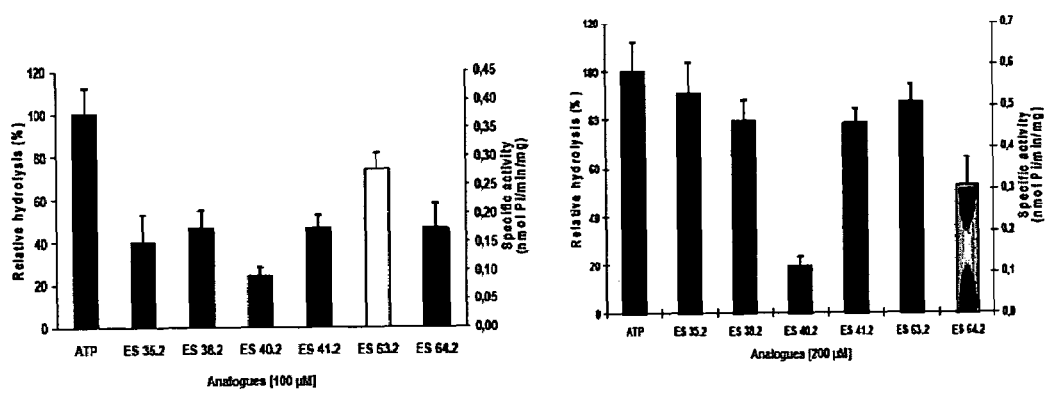
Fig. 7A
Fig. 7B

FLUORESCENT N²,N3-ETHENO-PURINE (2'-DEOXY) RIBOSIDE DERIVATIVES AND USES THEREOF

FIELD OF THE INVENTION

The present invention relates to fluorescent $N^2,N3$-etheno-purine (2'-deoxy) riboside derivatives, their preparation and uses thereof for staining DNA/RNA and for detection and quantitation of genetic material.

BACKGROUND OF THE INVENTION

Staining nucleic acids is an essential tool in the manipulation of genetic material for any detection or quantitation purpose. The natural bases of DNA are not useful as fluorescent probes because of their extremely low quantum yields, and thus the use of extrinsic probes is necessary.

A common methodology for a sensitive detection of DNA and RNA is the application of fluorescent dyes. The use of these dyes is an attractive alternative to radioactive oligonucleotide labels that require special laboratory facilities and constant precautions to avoid high radiation levels. Currently marketed dyes for nucleic acids staining include the following types of fluorescent markers: (i) intercalating dyes that are incorporated non-covalently to nucleic acids (e.g. cyanine dyes); (ii) minor groove-binding dyes; (iii) large hydrophobic fluorescent dyes (e.g. fluorescein, rhodamine) that are incorporated covalently to nucleotide (oligonucleotide) positions that do not interfere with base pairing (e.g. at the uracil C5, or at the 3'/5' ends of an oligonucleotide); and (iv) secondary detection method to amplify the signal using a dye or enzyme-labeled streptavidin to detect a biotinylated probe.

These dyes are used in various techniques for detecting genetic material in DNA arrays, gels, in virus particles, and in cells, by fluorescence microscopy or in electrophoresis gels visualized by epi-illumination. Although the above-mentioned fluorescent dyes are highly useful in the field of nucleic acids detection and quantitation, they suffer from many limitations regarding the preparation and application of nucleic acid probes.

Limitations regarding the preparation of nucleic acid probes include: (i) covalent/non-covalent labeling of (oligo) nucleotides by fluorescent dyes require additional experimental procedures involving the use of unique reagents and kits, prior to nucleic acid detection; (ii) various dyes (e.g. ethidium bromide) are chemical hazards; they are potent mutagens and must be handled with extreme care; (iii) various dyes are poorly soluble in water or in phosphate-buffered saline; (iv) in several labeling procedures, nucleotides are labeled by various fluorophores, and then enzymatically incorporated into RNA or DNA probes. In such chemical reactions, several differently labeled conjugates can be produced and hamper the fluorimetric analysis; (v) if measurements are done in solution, the unreacted dye, that has its own fluorescence, may complicate the spectroscopic analysis; (vi) a large hydrophobic dye attached to a nucleotide alters the efficiency of enzymatic incorporation. Thus, samples prepared from labeled nucleotides may have different levels of labeling, making it difficult to compare levels of hybridization between samples; (vii) labeling an oligonucleotide without enzymatic incorporation, e.g., by forming a coordination complex between the nucleic acid and Pt-containing label, results in the labeling of only one dye molecule per 12-20 bases and this labeling ratio may not be sufficient; (viii) a two-step protocol involving first the incorporation of a slightly modified nucleotide into nucleic acid, followed by covalent binding of fluorescent dyes, also suffers the limitation of a relatively small number of dye molecules that can be incorporated (1 dye molecule per 12-20 bases); and (ix) variation of fluorescence yield with degree of dye conjugation to the nucleic acid probe can significantly reduce the reliability of quantitative measures of hybridization-based assays.

Other limitations regarding the application of nucleic acid probes include: (i) the dye may stain other biopolymers; (ii) the use of those stains on gels may result in background fluorescence; and (iii) the intercalating dyes cannot distinguish between RNA and DNA.

An alternative approach to nucleobases staining has been proposed for improving the fluorescence of nucleobases by extension of the natural fluorophore. Adenine has poor fluorescence properties (Callis, 1983). However, bridging the adenine $N1,N^6$-positions by an etheno moiety, such as to obtain $N1,N^6$-etheno-adenosine of formula 1 (see appendix A herein, Y is OH), improves the fluorescence of the parent adenine system (e.g., for 1, $\lambda_{max}$ 415 nm, $\phi$0.6) (Secrist et al., 1972; Thomas and Leonard, 1976). Over the past three decades, $N1,N^6$-etheno-(2'-deoxy)adenosine (compounds of formula 1, wherein Y is H or OH; $\epsilon$-d-A/$\epsilon$-A), as well as other $\epsilon$-nucleobases such as $N3,N^4$-etheno-(2'-deoxy)cytidine (compounds of formula 2 in Appendix A, wherein Y is H or OH; $\epsilon$-d-C/$\epsilon$-C), and $N^2,N3$-etheno-(2'-deoxy)guanosine (compounds of formula 3 in Appendix A, wherein Y is H or oH; $\epsilon$-d-G/$\epsilon$-G), have been extensively studied as fluorescent nucleos(t)ide probes. All these probes bear an etheno bridge that represents minimal perturbation to the natural system (Leonard, 1984; Leonard, 1992).

$N1,N^6$-Etheno adenine nucleotides are commonly applied as fluorescent probes for various biochemical studies, such as: structure and function of nucleic acids, protein visualization, enzymatic studies, investigation of nucleotide binding-site, conformational analysis of nucleotides, and pharmacology of nucleosides/nucleotides.

Despite the improved fluorescence properties of 1, as compared to adenosine, its application as a fluorescent probe is limited due to the structural difference between 1 and the natural nucleoside. Thus, $N1,N^6$-$\epsilon$-A nucleo(s)tides can not be applied to biochemical systems requiring H-bonding based molecular recognition. Specifically, N1 and $N^6$-nitrogens are engaged in an imidazole ring, resulting in the loss of the adenine natural H-bonding capability. Consequently, there is reduction or loss of molecular recognition of these probes by target proteins or nucleic acids.

So far no fluorescent analogue of adenosine (or the corresponding nucleotides) having free $N1,N^6$-positions has been investigated nor disclosed.

SUMMARY OF THE INVENTION

Substituents that donate electrons to the $\pi$ system enhance absorption of light and increase fluorescence. Therefore, we considered improving the adenine fluorescence characteristics ($\phi$ and $\lambda_{max}$) by adding an amino substituent at C2-position and bridged $N^2$,N3-positions by an etheno bridge, to form the $N^2$,N3-etheno-adenosine of formula 4 (Appendix A), thus creating a conjugated fluorophore, while keeping the $N1,N^6$-positions free for H-bonding. In this way we generated several purine-riboside analogues suitable for fluorescence-based detection of genetic material upon hybridization with DNA/RNA.

The present invention thus relates to a compound of the formula I and oligonucleotides comprising one or more moieties thereof, said compound of formula I being of the formula:

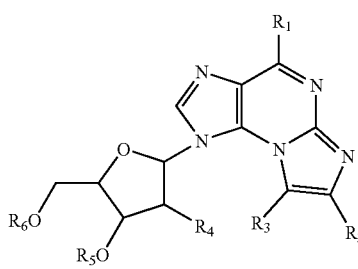

[I]

wherein

R₁ is —NHR₇, halo, —SR₇ or —N=CH—N(CH₃)₂;

R₂ and R₃, the same or different, each is H, hydrocarbyl, —NR₇R₈, —SR₇ or —OR₇;

R₄ is H or —OR₉;

R₅, R₆ and R₉ the same or different each is H, alkanoyl, PO₃²⁻, P₂O₆³⁻, P₃O₉⁴⁻; or R₅ is 2-cyanoethyl-N,N-diisopropyl-phosphoramidite and R₆ is 4,4'-dimethoxytrityl;

R₇ and R₈ the same or different each is H, hydrocarbyl or heterocyclyl;

and salts thereof.

The compounds of formula I and the oligonucleotides comprising one or more moieties of a compound of formula I are useful for detection and quantitation of DNA and RNA in biological genetic material. They are further useful as fluorescent probes of nucleic acids, adenosine-binding proteins and adenine nucleotide-binding proteins.

BRIEF DESCRIPTION OF THE FIGURES

FIG. 6 shows the dose response curves for ATP vs. analogues 30a and 30d at P2Y1 receptor stably expressed in HEK293 cells. ES 63.2 and ES 38.2 represent analogues 30a and 30d, respectively. F340/F380 represents the ratio between Ca²⁺ bound Fura-2 indicator and free indicator.

FIGS. 7A-7B show the rate of hydrolysis of ATP vs. analogues 30a-30f by Nucleoside Triphosphate Diphosphohydrolase, NTDPase 1 (7A) and 2 (7B). ES 63.2, ES 64.2, ES 35.2, ES 38.2, ES 40.2 and ES 41.2 represent analogues 30a, 30b, 30c, 30d, 30e and 30f, respectively.

DETAILED DESCRIPTION OF THE INVENTION

Figure 1:
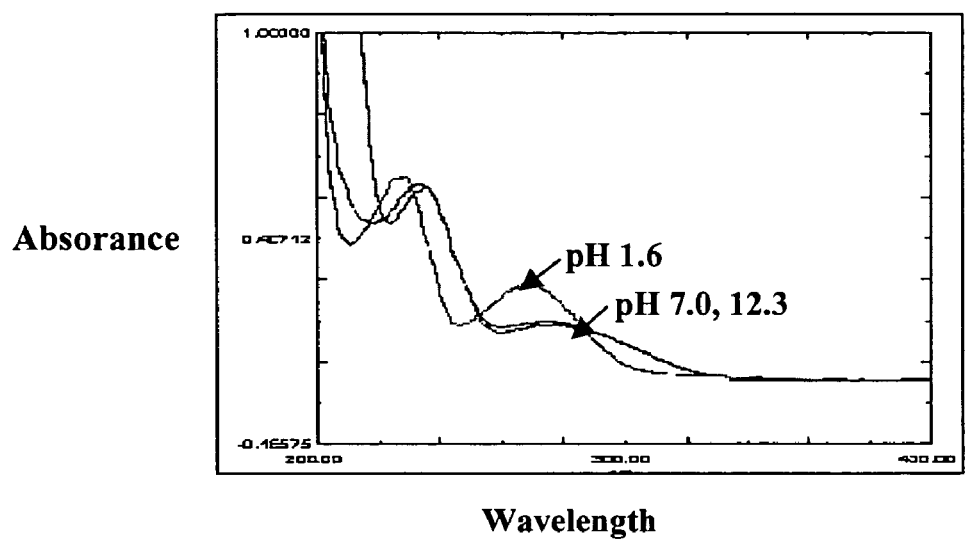
FIG. 1 shows the absorption spectra of N²,N3-ethenoadenosine (compound 4) at 4.85×10⁻⁵ M at several pH values (1.6, 7.0 and 12.3).
Figure 2:
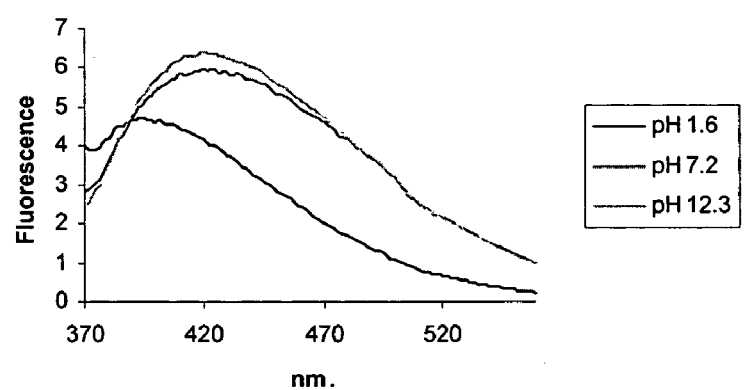
FIG. 2 shows the fluorescence spectra of N²,N3-ethenoadenosine (compound 4) at 4.85×10⁻⁵ M at several pH values (1.6, 7.2 and 12.3).

The present invention relates to the compounds of formula I and oligonucleotides comprising one or more moieties thereof, to their synthesis and uses thereof.

As used herein, the term "halo" includes fluoro, chloro, bromo, and iodo, and is preferably chloro or bromo, most preferably chloro.

The term "hydrocarbyl" in any of the definitions of the different radicals R, R', R₂ and R₃, includes a saturated or unsaturated, including aromatic, straight, branched or cyclic, including polycyclic, radical, containing carbon and hydrogen such as, but not being limited to, C₁-C₁₀ alkyl, C₂-C₁₀ alkenyl, C₂-C₁₀ alkynyl, C₃-C₁₀ cycloalkyl, (C₆-C₁₀) aryl and (C₆-C₁₀)ar(C₁-C₈)alkyl, and the aryl may be unsubstituted or substituted by one or more OH, C₁-C₄ alkyl, —O—(C₁-C₄)alkyl, or —S—(C₁-C₄)alkyl groups.

The term "C₁-C₁₀ alkyl" typically means a straight or branched hydrocarbon radical having 1-10 carbon atoms and includes, for example, methyl, ethyl, n-propyl, isopropyl, n-butyl, sec-butyl, isobutyl, tert-butyl, n-pentyl, 2,2-dimethylpropyl, n-hexyl, n-heptyl, n-octyl, n-nonyl, n-decyl, and the like. Preferred are C₁-C₆ alkyl groups, most preferably methyl. The terms "C₂-C₁₀ alkenyl" and "C₂-C₁₀ alkynyl" typically mean straight and branched hydrocarbon radicals having 2-10 carbon atoms and 1 double or triple bond, respectively, and include ethenyl, 3-buten-1-yl, 2-ethenylbutyl, 3-octen-1-yl, and the like, and propynyl, 2-butyn-1-yl, 3-pentyn-1-yl, and the like. The term "C₃-C₁₀ cycloalkyl" means a cyclic or bicyclic hydrocarbyl group such as cyclopropyl, cyclobutyl, cyclopentyl, cyclohexyl, adamantyl, bicyclo[3.2.1]octyl, bicyclo[2.2.1]heptyl, and the like. The term "(C₆-C₁₀) aryl" denotes a carbocyclic aromatic radical such as phenyl and naphthyl and the term "(C₆-C₁₀) ar(C₁-C₈)alkyl" denotes an arylalkyl radical such as benzyl and phenetyl. The aryl radical, both in the aryl and arylalkyl groups, may be substituted by one or more OH, C₁-C₄ alkyl, —O—(C₁-C₄)alkyl, or —S—(C₁-C₄)alkyl groups, preferably one or two methoxy groups.

The term "alkanoyl" as used herein refers to a C₁-C₁₀, preferably C₁-C₄, alkanoyl radical, most preferably, acetyl.

The term "heterocyclyl" as used herein refers to a radical derived from a 5- or 6-membered aromatic heterocyclic compound containing one or more O, S and/or N atoms such as, but not limited to, pyrrolyl, furyl, thienyl, imidazolyl, oxazolyl, pyridyl, pymidinyl, and the like.

When the radical R₁ is —SR₇ and R₇ is S-hydrocarbyl, the hydrocarbyl is preferably a C₁-C₆ alkyl, most preferably methyl, or an aryl, most preferably phenyl, or an aralkyl, most preferably benzyl, radical. In a most preferred embodiment, R₁ is SCH₃.

When the radical R₁ is —NHR₇ and R₇ is hydrocarbyl, the hydrocarbyl is preferably a C₁-C₆ alkyl, more preferably methyl or ethyl, or an aryl, most preferably phenyl, or an aralkyl, more preferably benzyl, radical, in which the phenyl radical may be substituted by alkyl or alkoxy. In preferred embodiments R is 2,4-dihydroxybenzyl or, more preferably, 2,4-dimethoxybenzyl.

It should be understood that when the compound has more than a substituent R₇, then the R₇s may be identical or different.

The compounds described in the specification, both the compounds of formula I, the starting compounds and intermediates, and known compounds, are herein identified by the Arabic numbers 1-30 in bold. The full chemical structures are depicted in Appendix A and Schemes 1-8 herein.

The compound 4 is also identified by the name $N^2,N3$-etheno-adenosine or by the abbreviation $N^2,N3$-ε-A, and the compound 3 is also identified by the name $N^2,N3$-etheno-guanosine or by the abbreviation $N^2,N3$-ε-G. The compound 23 is also identified by the name $N^2,N3$-etheno-2'-deoxy-adenosine.

In one more preferred embodiment of the invention, the compound of formula I is the compound wherein $R_1$ is $NH_2$, $R_4$ is OH, and $R_2$, $R_3$, $R_5$ and $R_6$ each is H, herein designated compound 4.

In another more preferred embodiment of the invention, the compound of formula I is the compound wherein $R_1$ is $NH_2$, and $R_2$, $R_3$, $R_4$, $R_5$ and $R_6$ each is H, herein designated compound 23.

In other embodiment, the compound of formula I is selected from the group consisting of: (i) the compound wherein $R_1$ is —$NHR_7$, $R_4$ is —$OR_9$, $R_7$ is 2,4-dihydroxy-benzyl, and $R_2$, $R_3$, $R_5$, $R_6$ and $R_9$ each is H (compound 14a); (ii) the compound wherein $R_1$ is —$NHR_7$, $R_2$ and $R_3$ each is H, $R_4$ is —$OR_9$, $R_7$ is 2,4-dimethoxybenzyl, and $R_5$, $R_6$ and $R_9$ each is acetyl (compound 14b); (iii) the compound wherein $R_1$ is —Smethyl, $R_2$, $R_3$, $R_5$ and $R_6$ each is H, and $R_4$ is —OH (compound 17); (iv) the compound wherein $R_1$ is —Smethyl, and $R_2$, $R_3$, $R_4$, $R_5$ and $R_6$ each is H (compound 22); (v) the compound wherein $R_1$ is —$NH_2$, and $R_2$, $R_3$, $R_4$ and $R_5$ each is H, and $R_6$ is $P_3O_9^{4-}$ (compound 26); (vi) the compound wherein $R_1$ is —$NH_2$, $R_4$ is OH, and $R_2$, $R_3$, and $R_5$ each is H, and $R_6$ is $P_3O_9^{4-}$ (compound 30a); (vii) the compound wherein $R_1$ is —N=CH—$N(CH_3)_2$ and $R_2$, $R_3$, $R_4$, $R_5$ and $R_6$ each is H (compound 27); (viii) the compound wherein $R_1$ is —N=CH—$N(CH_3)_2$, $R_2$, $R_3$, $R_4$ and $R_5$ each is H, and $R_6$ is 4,4'-dimethoxytrityl (compound 28); and (ix) the compound wherein $R_1$ is —N=CH—N$(CH_3)_2$, $R_2$, $R_3$, and $R_4$ each is H, $R_5$ is 2-cyanoethyl-N,N-diisopropylphosphoramidite, and $R_6$ is 4,4'-dimethoxytrityl (compound 29).

The present invention further provides a DNA or RNA oligonucleotide comprising one or more moieties of a fluorescent compound of formula I. The oligonucleotide length will depend on the proposed use and has at least 15 nucleotide moieties. Preferably, the oligonucleotide is a 15 to 60 mer. The fluorescent moiety of the compound I may be attached to the 3'- and/or to the 5'-terminus of the oligonucleotide sequence and/or incorporated into the oligonucleotide sequence at any adenine (A) position of the oligonucleotide. Thus, the labeled oligonucleotide of the invention contains at least one fluorescent moiety of compound I and a maximum of two moieties at the 3'- and 5'-termini plus moieties replacing all A positions of the oligonucleotide.

The compounds of formula I of the invention can be prepared by several different methods, as depicted in Schemes 1-8 and exemplified in the examples herein. In these methods, creation of an additional imidazole ring is carried out by the reaction of the starting purine (2'-deoxy) riboside with bromoacetaldehyde. Different derivatives may be obtained by the same methods starting from suitable compounds or introducing the desired groups during the synthesis by standard methods well-known in the art.

Extension of natural nucleobases to form fluorophores is achieved by treating the formers with α-halo-aldehyde, at pH 4.5 (Secrist et al., 1972). For instance, the fluorescent angular isomer, $N^2,N3$-ε-G, 3, (emission maximum in water at 410 nm) is obtained from $O^6$-benzyl-guanosine and bromoacetaldehyde at pH 4.5 (Kusmierek et al., 1987). However, at an elevated pH, a non-fluorescent (Sattsangi et al., 1977; Kusmierek et al., 1992) linear isomer, $N1,N^2$-ε-G, 5, is obtained from guanosine (Boryski, 1990).

Since we targeted the novel angular heterocyclic system $N^2,N3$-ε-A, 4, rather than the related angular $N1,N^6$-ε-A 1, or linear $N1,N^2$-ε-A isomers, we had to direct the regiochemistry of the ring closure to $N^2,N3$-rather than to the $N1,N^6$- or $N1,N^2$-positions. For this purpose, we selected 6-Cl—, 6-NHAr-, or 6-SMe-purine riboside analogues as starting materials that would direct the reaction with bromoacetaldehyde, at pH 4.5, to the purine $N^2,N3$-positions. With these starting materials, we developed several efficient syntheses of the target compound 4 and its analogues (Schemes 1-4).

In one embodiment of the invention, $N^2,N3$-etheno-adenosine, 4, is prepared by novel short (3-4 steps), facile, and regiospecific syntheses, starting from 2-amino-6-chloro-purine riboside, 6 (Schemes 1, 2 and 4) or 2-amino-6-methylthio-purine riboside, 16 (Scheme 4). These syntheses provide the product in a reasonable yield and absolute regiospecificity. The key step in the preparation of 4 was the treatment of 6-SMe or 6-Cl purine riboside with bromoacetaldehyde at pH 4.5 and 38° C.

Thus, in the first synthesis (depicted in Scheme 1), 6-chloro-2-amino-purine riboside, 6, was treated with freshly prepared bromoacetaldehyde at pH 4.5, at 38° C. for 30 h. $N^2,N3$-ε-guanosine 3 was obtained in 86% yield. Initially, $N^2,N3$-ε-6-chloro-purine riboside was formed, and then hydrolyzed to the corresponding guanosine derivative 3. Apparently, the imidazole ring formation is faster than the hydrolysis of the chloro substituent, as guanosine is not reactive at all with α-haloaldehyde at pH 4.5 (Sattsangi et al., 1977).

The replacement of the C6 carbonyl oxygen in 3 by $NH_2$ is achieved in three steps: 1. The ribose hydroxyls are per-acetylated to provide product 7; 2. This product is then chlorinated by phosphoryl chloride in the presence of N,N-dimethylaniline to provide 8; 3. Finally, 8 was treated with ethanolic $NH_3$ at 100° C. to provide product 4.

The moderate yield of the chlorination step prompted us to explore more drastic conditions for this conversion (Kusmierek et al., 2000). Thus, 7, in neat $SOCl_2$ solution and one drop of DMF, was heated at 100° C. for 3 h. Product 9 was obtained almost quantitatively, resulting from the reaction of 7 with a Vilsmeier reagent formed in-situ from thionyl chloride and DMF (Kikugawa et al., 1971). Likewise, the reaction of 7 in neat phosphoryl chloride solution in the presence of N,N-dimethylaniline and tetraethylammonium chloride at 120° C. for 3 h, resulted in the quantitative formation of product 10, due to the attack of N,N-dimethylaniline on the initially formed chloro product 8.

To avoid the loss of the chloro substituent at C6, due to its hydrolysis (conversion of 6 to 3), we attempted the $N^2,N3$-ring closure reaction under anhydrous conditions. Instead of the aqueous bromoacetaldehyde reagent solution, we attempted in-situ generation of the aldehyde under anhydrous conditions in dry acetonitrile from bromoacetaldehyde diethyl acetal, $BF_3$:etherate, and NaI under reflux (Mandal et al., 1986). Per-acetylated 2-amino-6-chloro-purine riboside, 12, was then added to the solution at 38° C., giving rise to a complex mixture of products.

Therefore, instead of working under anhydrous conditions, we repeated the reaction of 6 with bromoacetaldehyde in a two-phase system —$CHCl_3$:buffer (pH 4.5), Scheme 2. To increase the solubility of 6 in chloroform solution, we used 2',3',5'-triacetylated-2-amino-6-chloropurine riboside 12 obtained by chlorination of per-acetylated guanosine 11, or acetylation of 6. Thus, bromoacetaldehyde and the phase-transfer catalyst, tetrabutylammonium bromide, were added to 12 in CHCl$_3$-EtOH-buffer (pH 4.5) at 38° C. for 48 h. The desired product, 8, was obtained in a 38% yield as the major product. In addition, etheno-guanosine analogue 7, was obtained in an 8% yield. This minor product was converted back to 8 in neat POCl$_3$ solution in the presence of N,N-dimethylaniline at 120° C. for 20 min. Heating product 8 in ethanolic ammonia solution replaced C6-chloro by amine, and removed the acetate protective groups to furnish 4 in a reasonable yield.

To improve the overall yield of 4, we attempted alternative pathways (Schemes 3, 4). The first approach involved the early substitution of the C6-Cl by an aryl amine to yield 13, followed by reaction with bromoacetaldehyde to form etheno analogue 14, and finally, attempted removal of the N$^6$-amine protecting group to produce 4.

As an amine protective group, we selected 2,4-dimethoxy-benzyl, due to its relatively mild removal conditions as compared to those of N-benzyl group. Our preliminary attempts to remove a benzyl protective group from N$^6$-exocyclic amine in 14a included hydrogenation at 70 psi, over Pd/C with or without HOAc, and oxidation of the benzyl carbon by RuO$_2$/NaIO$_4$ or NH$_4$S$_2$O$_8$. However, these attempts were unsuccessful, as 14a remained unchanged under hydrogenation conditions, and oxidation with persulfate caused complete cleavage of the etheno-bridge. Alternatively, 12 was treated with 2,4-dimethoxy-benzylamine in EtOH to provide 13b in excellent yield. Product 13b was in turn treated with bromoacetaldehyde, as described above, to provide, regiospecifically, the angular etheno product, 14b, in a good yield. However, the attempted removal of the aryl protective group by 2,3-dichloro-5,6-dicyano-1,4-benzoquinone (DDQ) oxidation of 14b in CHCl$_3$/H$_2$O caused complete cleavage of both the glycosidic bond and the etheno bridge in 14b, whereas the 2,4-di-OMe-benzyl-amino group remained intact.

Nonetheless, nucleotide analogues of 14a,b and c (the latter was prepared from 12 and dibenzylamine) were synthesized to evaluate their molecular recognition by our target proteins.

The most convenient synthetic approach (Scheme 4), involved the substitution of SMe group at C6 of the purine ring, 16, for both directing the ring cyclization to N$^2$,N3-positions, and facilitating eventually the substitution of C6 by an amine.

Compound 16 was prepared by treating 6 with NaSMe in DMSO. Alternatively, 16 was obtained in a high yield by methylation of thioguanosine, 15. Bromoacetaldehyde solution was added to 16 in CHCl$_3$/EtOH/water, at pH 4.5, at 38° C. to provide the etheno product 17 in a reasonable yield and absolute regiospecificity. Finally, product 17 was treated with ethanolic ammonia at 150° C. to provide product 4.

The synthetic procedures of the invention proved highly efficient not only for the formation of the novel angular analogue N$^2$,N3-ε-A, 4, but also for the known N$^2$,N3-ε-G, 3. Thus, the method for the preparation of N$^2$,N3-ethenoguanosine, 3, by reaction of 6-chloro-2-amino-purine riboside with bromoacetaldehyde, as depicted in Scheme 1, is also encompassed by the present invention. According to this method, N$^2$,N3-ε-G was obtained in 86% yield, while in earlier syntheses it was obtained in 25-48% yield (Kusmierek et al., 1987; Khazanchi et al., 1993).

The compound N$^2$,N3-ε-A, 4, is fluorescent ($\lambda_{max}$ 420 nm in water, φ0.03), and has similar fluorescence properties to those of the known N$^2$,N3-ε-G, 3, and N1,N$^6$-ε-A, 1 (Secrist et al., 1972). However, unlike the latter, analogue 4 exhibits significant fluorescence even at acidic pH. The related analogue, N$^2$,N3-ε-6-methylthio-purine riboside, 17, exhibits remarkable fluorescence ($\lambda_{max}$ 520 nm in water, φ0.15).

Since creation of an additional imidazole ring in the related known guanine base, N$^2$,N3-ε-G, 3, has only a moderate effect on its base-stacking ability (Glemarec et al., 1991), it can be expected for N$^2$,N3-ε-A, 4, the same base stacking ability as for adenine. Furthermore, unlike N1,N$^6$-ε-A 1, analogue 4 conserves the original adenine H-bonding pattern.

The synthesis of N$^2$,N3-ε-2'-deoxy-A, 23, presents a greater synthetic challenge, as N3-substituted 2'-deoxy-purine-nucleosides possess an extremely labile glycosidic bond (Kung and Jones, 1991). Indeed, the related N$^2$,N3-ε-2'-deoxy-G analogue could not be prepared under acidic conditions at 38° C., as the glycosidic bond of deoxynucleosides is hydrolyzed 100-1000 times more readily than that of ribonucleosides.

Two synthetic solutions were previously proposed to overcome the instability of the glycosidic bond in N3-substituted 2'-deoxypurine nucleosides (Kung and Jones, 1991). One solution involved the preparation of N$^2$,N3-ε-2'-deoxy-G from 2'-deoxy-G-5'-monophosphate, instead of the corresponding nucleoside. The reason for that was the higher solubility of the nucleotide in the reaction medium and higher stability (ca. 3-fold) of the nucleotide glycosyl bond at pH 6-8. Furthermore, their synthetic scheme involved slightly basic pH (7.5-8.5). However, this pH value causes ring cyclization with bromoacetaldehyde at N1 and N$^2$ positions of the guanine ring. To control the cyclization regiochemistry at N$^2$,N3-positions, the authors had used O$^6$-benzyl-2'deoxy-G-5'-monophosphate as the starting material. In this way, preparation of N$^2$,N3-ε-2'-deoxy-G involved extra synthetic steps such as O$^6$-benzylation, 5'-phosphorylation, and finally, O$^6$-de-benzylation, and enzymatic 5'-de-phosphorylation. The overall yield after 7 synthetic steps was extremely low.

The second synthetic solution involved the preparation of N$^2$,N3-ε-2'-deoxy-G under acidic conditions from the O$^6$-benzyl-guanosine, followed by 2'-deoxygenation. The desired product was obtained after 8 synthetic steps, from guanosine, in 7.5% yield (Khazanchi et al., 1993).

In contrast, our synthesis of N$^2$,N3-ε-2'-deoxy-A, 23, according to the present invention, involved only 4 synthetic steps starting from either 2'-deoxy-G or 2'-deoxy thio-G (Scheme 6). Specifically, 6-methylthio-purine-2'-deoxy-riboside, 21, was prepared from 2'-deoxy-G, 19, by trifluoroacetic acid anhydride (TFAA) activation, followed by treatment with sodium thiomethoxide (NaSCH$_3$) in pyridine (Kung and Jones, 1991). A superior method was the preparation of 21 in 85% yield upon treatment of 6-thioguanosine, 20, with NaOH and MeI, as described before for 6-thioinosine (Jack, 1958).

We targeted 21 as the starting material for the preparation of the ethenonucleoside 23, as the 6-SMe group served both as an activator of the purine ring for the N$^2$,N3-ring cyclization, and as a precursor of the amino group at C6.

The key step in the synthesis of 23 is the ring cyclization reaction. For the corresponding ribo analogue (6-SMe-purine riboside) we devised a 2-phase reaction conditions involving NH$_4$HCO$_3$/HCl buffer (pH 4.8) and CHCl$_3$ at 25° C. for 36 h, resulting in the formation of the product in 38% yield as one exclusive regioisomer As the glycosidic bond in 2'-deoxy-nucleosides, and especially in N3-substituted 2'-deoxy-nucleosides, is significantly less stable than that of the corresponding ribo nucleosides, we realized that the acidic conditions (pH 4.5, 38° C.) we previously used for the preparation of compound 4 cannot be applied here. Indeed, reaction of 21 at pH 4.5 at room temperature (instead of 38° C.), resulted in 28% yield of product 23, accompanied by hydrolysis products.

Raising the reaction pH to 6 resulted in a mixture of 6-SMe-$N^2$,N3-$\epsilon$-2'-deoxy-purine riboside, 22, and 6-SMe-N1,$N^2$-$\epsilon$-2'-deoxy-purine riboside, 24, products (see Scheme 7). Lowering the reaction pH to 5 improved 22:24 ratio (36:2%). The optimal pH value was exactly 4.8. At this pH the desired product was formed at 38% yield with no 24 as a side-product.

Having optimized this key reaction, we set to replace the 6-SMe group by an amino group. Although a related $N^2$,N3-$\epsilon$-2'-deoxy-G is known to survive the treatment with concentrated ammonia at room temperature, we suspected the stability of 22 and 23 at the conditions required to displace SMe by amine (2M $NH_3$/EtOH at 100° C. for 24 h). Surprisingly, both compounds 22 and 23 survived these drastic conditions and product 23 was obtained in 46% yield.

The oligonucleotides of the invention are prepared by using one or more moieties of an autofluorescent compound of formula I by chemical, automated, and oligonucleotide synthesis, via phosphoramidite technology, to produce labeled oligonucleotide probes. For this purpose, suitable phosphoramidite intermediates as the compound 29 can be used as building blocks.

Alternatively, the 5'-triphosphate nucleosides of the invention, i.e., the compounds wherein $R_6$ is $P_3O_9^{4-}$, can be incorporated into RNA or DNA probes, using RNA/DNA polymerases to produce fluorescently labeled oligonucleotide probes. Likewise, these fluorescent nucleotides can be attached at the ends of a nucleic acid probe using RNA/DNA ligases.

The compounds of formula I are fluorescent and constitute a further extension of the natural fluorophore with improved properties for use as fluorescent agents for staining DNA and RNA. They can, thus, be used for detection and quantitation of DNA and RNA in DNA arrays and DNA electrophoresis gels, and in biological material such as microorganism cultures, virus particles, cell and tissue samples, by methods well-known in the art, for example, by fluorescence microscopy or more sophisticated detection devices such as laser-excited confocal fluorescence gel scanner.

Likewise, the oligonucleotide probes of the invention can be used for detecting the presence and quantitating a nucleic acid sequence in a sample methods well-known in the art, The probe is designed to have the complementary sequence to the tested nucleic acid sequence. The fluorescence of the hybridized product, upon exposure to an exciting radiation, detects the presence of the nucleic acid sequence.

Among the several applications, the fluorescent dyes and probes of the invention can be used in detection and screening of genetic disorders, viruses, pathogenic microorganisms, diagnostic markers for cancer, PCR-based forensic identity tests, monitoring gene expression, monitoring the effectiveness of gene therapy pharmaceuticals and further biotechnological and scientific applications.

In contrast to the known N1,$N^6$-etheno-adenine nucleotides, the $N^2$,N3-etheno-adenosine molecules of the invention have free N1,$N^6$-positions available for base pairing via H-bonding, thus enabling normal hybridization of the oligonucleotide probe with nucleic acid of interest.

The invention will now be illustrated by the following non-limiting Examples.

EXAMPLES

Experimental (i) General

New compounds were characterized and resonances assigned by proton and carbon nuclear magnetic resonance using Bruker AC-200/AC-300 NMR spectrometers. HOD signal was used as a reference, at 4.78 ppm, for samples in $D_2O$. Nucleoside derivatives were characterized by electron spray ionization mass spectrometry (ESI/MS) on a Q-TOF micro mass spectrometer (Micromass-Waters, Corp.). High-resolution mass spectra were obtained using Apex III Bruker mass spectrometer (ESI/MS).

Bromoacetaldehyde used for the synthesis of the etheno derivatives was prepared as follows: A mixture of bromoacetaldehyde diethyl acetal (5 ml), 1 M HCl (15 ml) and ethanol (5 ml) was stirred for 3 days at 37° C. No phase separation occurs when the mixture is brought to room temperature. The final solution contains approximately 1.3 mmol bromoacetaldehyde in 1 ml. For the preparation of the etheno-products we used a $NH_4HCO_3$/HCl buffer, pH 4.5. This buffer proved superior to the commonly used NaOAc/HOAc, as the former one is removed by freeze-drying and enables simple and easy purification of the etheno-product.

Chlorination and amination were performed in flame-dried flasks under Ar atmosphere. Reagents were pre-dried in vacuum oven overnight. $POCl_3$ and acetonitrile were freshly distilled. Aromatic amines were freshly distilled. DMSO was dried over activated molecular sieves 4A.

Thioguanosine (PR 3845) was purchased from Berry & Associates, Inc.

(ii) Synthesis of $N^2$,N3-etheno-guanosine ($N^2$,N3-$\epsilon$-G), 3

2-(4-(O-benzyl)-1H-imidazo[2,1-e]purine-1-yl)-tetrahydro-5-(hydroxymethyl)-furan-3,4-diol As depicted in Scheme 1, step a, bromoacetaldehyde (0.9 ml of about 1.3 M solution, 6 eq) was added to a solution of 6-chloro-2-amino-purineriboside, 6 (50 mg, 0.16 mmol) in a mixture of $NH_4HCO_3$/HCl buffer (6 ml), pH 4.5, and EtOH (3 ml). The reaction mixture was stirred at 38° C. for 30 h. The mixture was evaporated in vacuo to about half-volume and EtOH was removed. A few drops of saturated sodium bicarbonate aqueous solution were added to neutralize the mixture (pH 8). The mixture was diluted by water (100 ml) and freeze-dried. The product was purified on silica-gel column and eluted with $MeOH:CHCl_3$ (1:1). Product 3 was obtained as a white solid in 86% yield (44 mg). $^1H$ NMR (600 MHz, $D_2O$): 8.03 (s, 1H, H-8); 7.40 (d, 1H, etheno); 7.21 (d, 1H, etheno); 5.89 (d, 1H, H-1'); 4.75 (t, 1H, H-2'); 4.42 (t, 1H, H-3'); 4.23 (m, 1H, H-4'); 3.9 (dd, 1H, H-5'); 3.83 (dd, 1H, H-5') ppm. $^{13}C$ NMR (600 MHz, $D_2O$): 153.06 (C-6); 150 (C-4); 145.52 (C-2); 139.68 (C-8); 115.78 (C-5); 107.53 (etheno); 117.62 (etheno); 88.74 (C-1'); 85.92 (C-4'); 73.95 (C-2'); 71.16 (C-3'); 62.14 (C-5') ppm. MS m/z: 307 ($MH^+$).

The predominant tautomer for $N^2$,N3-$\epsilon$-G is the oxo-form, where the labile proton is attached to N8 (Glemarec et al., 1991). $N^2$,N3-$\epsilon$-G should possess, in protonated form, H-bonding characteristics like guanine (Sattsangi et al., 1977). However, since the $pK_a$ of $N^2$,N3-$\epsilon$-G is 2.11 (Glemarec et al., 1991), this compound is not expected to form canonical Watson-Crick H-bonds with other bases under physiological conditions. Yet, $N^2,N3$-ϵ-G is known to base pair with both cytosine and thymine during in vitro DNA synthesis, thus, specifically inducing G→A transitions during DNA replication in *E. coli* (Cheng et al., 1991).

(iii) Synthesis of 2',3',5'-tri-O-acetyl-$N^2$,N3-etheno-guanosine, 7

2-(4-(oxo)-1H-imidazo[2,1-e]purine-1-yl)-tetrahydro-2,3,5-tri-O-acetylatedl)-furan As depicted in Scheme 1, step b, $N^2$,N3-etheno-guanosine, 3 (200 mg, 0.58 mmol) was added to a mixture of pyridine (0.8 ml) and acetic anhydride (124 µL, 8 eq). The reaction mixture was stirred at room temperature for 48 h. Pyridine and acetic acid were evaporated in vacuo. The residue was washed 4 times with EtOH and purified on a silica-gel column eluted with MeOH:$CHCl_3$ (1:1). The solvent was removed by evaporation. Product 7 was obtained as yellow oil in 63% yield (178 mg). $^1$H NMR (600 MHz, $CHCl_3$): 7.90 (s, 1H, H-8); 7.67 (d, 1H, etheno); 7.26 (d, 1H, etheno); 6.03 (d, 1H, H-1'); 6.10 (t, 1H, H-2'); 5.80 (t, 1H, H-3'); 4.42 (m, 1H, H-4'); 4.39 (m, 1H, H-5'); ppm. $^{13}$C NMR (600 MHz, $CHCl_3$): 170.87 ($CH_3$); 169.85 ($CH_3$); 169.54 ($CH_3$); 151.63 (C-6); 146.00 (C-4); 145.90 (C-2); 137.58 (C-8); 114.94 (C-5); 107.57 (etheno); 115.91 (etheno); 87.07 (C-1'); 79.82 (C-4'); 72.31 (C-2'); 70.58 (C-3'); 63.03 (C-5'); 20.72 (CO); 20.55 (CO); 20.44 (CO) ppm. MS m/z: 434 ($MH^+$).

(iv) Chlorination of Compound 7 Under Drastic Conditions

In one experiment, $SOCl_2$ (1 ml) was added to a solution containing pre-dried 7 (70 mg, 0.16 mmol) and 1 drop DMF. The reaction flask was placed in an oil bath preheated to 100° C. for 3 h. The residue was dissolved in $CH_2Cl_2$ and stirred vigorously with crushed ice. The layers were separated and the organic phase washed with 5% $NaHCO_3$ (5 ml), dried over $MgSO_4$, and filtered. The solvent was evaporated in vacuo. Product 9 (Scheme 1a) was obtained in a quantitative yield. MS m/z: 522 ($MH^+$).

In another experiment, N,N-dimethylaniline (21 µL, 1 eq) and phosphoryl chloride (91 µL, 6 eq) were added to pre-dried 7 (70 mg, 0.16 mmol) and pre-dried tetraethylammonium chloride (53 mg, 2 eq) at room temperature. The reaction flask was placed in an oil bath preheated to 120° C. and the solution was heated with stirring under reflux for 3 h. Volatile materials were evaporated in vacuo. The residue was dissolved in $CHCl_3$ (5 ml) and stirred vigorously with crushed ice for 15 min. The layers were separated and the aqueous phase was extracted with $CHCl_3$ (3×5 ml). The combined organic phase was kept cold by addition of crushed ice. The organic phase was washed with cold water (6×5 ml), 5% $NaHCO_3$ (5 ml), water (2×5 ml), to pH 7. The organic phase was dried over $MgSO_4$, filtered, and the solvent was evaporated in vacuo. Product 10 (Scheme 1a) was obtained in a quantitative yield. MS m/z: 537 ($MH^+$).

(v) Synthesis of $N^2$,N3-Etheno-6-chloro-2',3',5'tri-O-acetyl-purine riboside, 8

2-(4-(chloro)-1H-imidazo[2,1-e]purine-1-yl)-tetrahydro-2,3,5-tri-O-acetylatedl)-furan As depicted in Scheme 1, step c, phosphoryl chloride (448 µL, 6 eq) and N,N-dimethylaniline (101 µL, 1 eq) were added to a solution of pre-dried 2',3',5'-tri-O-acetylated-$N^2$,N3-ethenoguanosine, 7 (347 mg, 0.81 mmol) in dry acetonitrile (3 ml). The reaction flask was then placed in an oil bath preheated to 70° C. and the solution was heated with stirring for 1 h. Volatile materials were then evaporated immediately in vacuo. The residue was dissolved in $CHCl_3$ (5 ml) and stirred vigorously with crushed ice for 15 min. The layers were separated and the aqueous phase was extracted with $CHCl_3$ (3×5 ml). The combined organic phase was kept cold by the addition of crushed ice and washed with cold water (6×5 ml), 5% $NaHCO_3$ (5 ml), water (2×5 ml) to pH 7. The organic phase was dried over $MgSO_4$ and filtered. The solvent was evaporated in vacuo. Product 8 was obtained as a yellow oil in 45% yield (154 mg). MS m/z: 452 ($MH^+$).

(vi) 2-Phase Synthesis of $N^2$,N3-etheno-6-chloro-2',3',5'-tri-O-acetyl-purine riboside, 8

As depicted in Scheme 2, step b, bromoacetaldehyde (1.3 M, 3.2 ml, 6 eq) and phase transfer catalyst, tetrabutylammonium bromide (2 eq) were added to 2',3',5'-triacetylated-2-amino-6-chloropurine riboside, 12 (300 mg, 0.7 mmol) dissolved in $CHCl_3$ (10 ml) and EtOH (15 ml). pH of the reaction was adjusted to 4.5 throughout the entire reaction time by the drop-wise addition of 1 M $NH_4HCO_3$ and 10% HCl solutions. The reaction mixture was stirred at 38° C. for 48 h. At the end of the reaction a few drops of saturated sodium bicarbonate aqueous solution were added to neutralize the mixture (pH 8). Water (100 ml) was added to the reaction mixture followed by freeze-drying and purification on a silica-gel column (elution with $CHCl_3$). Product 8 was obtained in 38% yield (12 mg) as yellow oil. In addition, product 7 was isolated as a by-product in 8% yield (2.4 mg) as a white solid. $^1$H NMR (300 MHz, $CDCl_3$): 7.97 (d, 1H, etheno); 7.26 (d, 1H, etheno); 5.98 (d, 1H, H-1'); 5.91 (t, 1H, H-2'); 4.42 (t, 1H, H-3'); 4.23 (m, 1H, H-4'); 3.9 (dd, 1H, H-5'); 3.61 (dd, 1H, H-5'); 2.10-2.12 (s, 9H, $CH_3CO$) ppm. $^{13}$C NMR (600 MHz, $CDCl_3$): 170.28 (C-6); 169.47 (CO); 169.44 (CO); 169.24 (CO); 150 (C-4); 145.52 (C-2); 139.68 (C-8); 115.78 (C-5); 107.53 (etheno); 117.62 (etheno); 88.74 (C-1'); 85.92 (C-4'); 73.95 (C-2'); 71.16 (C-3'); 62.14 (C-5') ppm. MS m/z: 452 ($MH^+$).

(vii) Synthesis of 2',3',5'-tri-O-acetyl-6-chloro-2-amino-purine riboside, 12

5-(2-amino-6-(chloro)-9H-purine-9-yl)-tetrahydro-2,3,5-tri-O-acetylated-furan

As depicted in Scheme 2, step a, 2-amino-6-chloro-purine riboside, 6 (300 mg, 1 mmol) was dissolved in a mixture of pyridine (2 ml) and acetic anhydride (94 µL, 4 eq). The reaction mixture was stirred at room temperature for 48 h. Pyridine and acetic acid were evaporated in vacuo. The residue was washed 4 times with EtOH and purified on silica gel column (elution with diethylether and EtOAc, 2.5:1). Product 12 was obtained as white solid in 68% yield (287 mg). $^1$H NMR (200 MHz, $CDCl_3$): 7.97 (s, H-8); 7.59 (d, 1H, etheno); 7.05 (d, 1H, etheno); 6.41 (m, 2H, H-1', H-2'); 5.80 (t, 1H, H-3'); 5.40 (m, 1H, H-4'); 4.35 (dd, 1H, H-5'); 4.07 (dd, 1H, H-5'); 2.10-2.12 (s, 9H, $CH_3CO$) ppm. MS m/z: 428 ($MH^+$).

Alternatively, product 12 was obtained by chlorination of per-acetylated guanosine 11, as shown in Scheme 2: N,N-dimethylaniline (1.55 ml, 1 eq) and phosphoryl chloride (6.83 ml, 6 eq) were added to pre-dried per-acetylated guanosine (5 g, 0.012 mmol) in dry acetonitrile (25 ml). The flask was then placed in an oil bath preheated to 70° C. and the solution was heated with stirring for 1 h. Volatile materials were evaporated immediately in vacuo. The residue was dissolved in $CHCl_3$ (50 ml) and stirred vigorously with crushed ice for 15 min. The layers separated and the aqueous phase was extracted with $CHCl_3$ 5 times. The combined organic phase was kept cold by addition of crushed ice. It was then washed with cold water, 5% $NaHCO_3$, and water to pH 7. The organic phase was dried over $MgSO_4$, filtered, and the solvent was evaporated in vacuo. The residue was purified on a silica-gel column eluted with 7:3 EtOAc:diethyl ether. Product 12 was obtained as a white solid in 49% yield (2.6 g).

(viii) Synthesis of 2',3',5'tri-O-acetyl-6-(2,4-dimethoxybenzylamino)-2-amino-purine riboside, 13b As depicted in Scheme 3, step a, 2,4-dimethoxybenzylamine (70 µL, 2 eq) was added to 2',3',5'-tri-O-acetyl-6-chloro-2-amino-purine riboside, 12 (100 mg, 0.23 mmol) in EtOH (30 ml). 2,4-Dimethoxybenzyl was selected as the amino protective group due to its facile removal as compared to the extremely difficult removal of N-benzyl group. The reaction mixture was heated at 60° C. for 36 h. TLC ($CHCl_3$:MeOH, 9:1) indicated that the reaction was completed, showing a new spot at $R_f$=0.82. The solution was concentrated under reduced pressure. The crude product was purified by flash column chromatography on silica gel using $CHCl_3$:MeOH and 95:5 as the eluent. Product 13b was obtained as with solid in 91% yield (110.9 mg). $^1$H NMR (200 MHz, $CD_3OD$): 7.86 (s, 1H, H-8); 7.57 (m, 2H, benzyl); 7.30 (s, 1H, benzyl); 6.41 (d, 1H, H-1'); 5.98 (t, 1H, H-2'); 5.84 (t, 1H, H-3'); 5.27 (s, $CH_2$); 4.36 (m, 2H, H-4', H-5'); 3.86 (s, $CH_3$); 3.77 (s, $CH_3$); 2.07-2.11 (9H, $CH_3$) ppm. MS m/z: 559 ($MH^+$).

(ix) Synthesis of 2',3',5'-tri-O-acetyl-6-(2,4-dimethoxybenzylamino)-$N^2$,N3-etheno-purine riboside, 14b As depicted in Scheme 3, step b, product 13b was treated with bromoacetaldehyde to provide regiospecifically the angular etheno product, 14b. The reaction conditions were the same as for product 8, (see vi above) starting from 0.30 mmol product 13b. The reaction mixture was stirred at 38° C. for 20 h. Product 14b was obtained as a white solid in 75% yield (68 mg). $^1$H NMR (300 MHz, $CD_3OD$): 8.436 (s, 1H, H-8); 8.02 (d, 1H, etheno); 7.73 (d, 1H, etheno); 6.95 (m, benzyl); 6.14 (d, 1H, H-1'); 5.67 ($CH_2$); 4.96 (s, $CH_3$); 4.80 (s, $CH_3$); 4.71 (t, 1H, H-2'); 4.43 (t, 1H, H-3'); 4.17 (m, 1H, H-4'); 3.88 (dd, 1H, H-5'); ppm. $^{13}$C NMR (300 MHz, $CD_3OD$): 154.18 (C-6); 131.99 (C-4); 142.60 (C-2); 125.31 (C-8); 121.46 (C-5); 113.77 (etheno); 108.18 (etheno); 89.76 (C-1'); 62.82 (C-4'); 87.22 (C-2'); 75.75 (C-3'); 72.03 (C-5'); 56.30 (s, $CH_3$); 49.56 (s, $CH_3$) 44.71 (benzyl) 49.85-48.15 (m, benzyl); 128.63-129.20 (benzyl) ppm. MS m/z: 583 ($MH^+$).

Attempts were made to remove the $N^6$-amine protecting group in order to produce compound 4. Our preliminary attempts to remove the 2,4-dihydroxybenzyl protective group from $N^6$-exocyclic amine in 14a included hydrogenation at 70 psi, over Pd/C with or without HOAc (Chi and Emile, 1984; Campbell et al., 1986), and oxidation of the benzyl carbon by $RuO_2/NaIO_4$ (Simon and Vinod, 1988) or $NH_4S_2O_8$ (Guillermo et al., 2002). However, these attempts were unsuccessful, as 14a remained unchanged under hydrogenation conditions, and oxidation with persulfate caused complete cleavage of the etheno-bridge. Therefore, we selected 2,4-dimethoxy-benzyl group to protect the $N^6$-exocyclic amine as its removal is usually achieved under milder conditions. However, DDQ oxidation (Michael and Jean, 1998) of 14b in $CHCl_3/H_2O$, or catalytic hydrogenation did not afford 4, although the etheno structure of 14b was conserved.

(x) Synthesis of 6-methylthio-2-amino-purine riboside, 16

5-(2-amino-6-(methylthio)-9H-purine-9-yl)-tetrahydro-2-(hydroxymethyl)furan-3 4-diol As depicted in Scheme 4, step b, sodium thiomethoxide (138 mg, 1.97 mmol, 3 eq) was added to a solution of 6-chloro-2-amino-purine riboside, 6 (200 mg, 0.66 mmol) in dry DMSO (6 ml). The solution was stirred at 60° C. for 40 h. A new spot on TLC (8:2 $CHCl_3$:MeOH) at $R_f$=0.53, indicated the formation of product 16. The solvent was evaporated in vacuo and the crude residue was purified on a silica-gel column (elution with $CHCl_3$:MeOH 95:5). Product 16 was obtained in 26% yield (53.6. mg) as lightly yellow solid. $^1$H NMR (200 MHz, $CDCl_3$): 8.19 (s, H-8); 5.87 (d, 1H, H-1'); 4.69 (t, 1H, H-2'); 4.30 (t, 1H, H-3'); 4.12 (m, 1H, H-4'); 3.82 (dd, 1H, H-5'); 3.78 (dd, 1H, H-5'); 2.610(s, $CH_3$) ppm. MS m/z: 314 ($MH^+$).

Alternatively, and as depicted in Scheme 4, step a, 6-thioguanosine 15 (300 mg, 1 mmol) was added to a stirred solution of 0.4 M sodium hydroxide (2.55 ml) for 10 min, followed by gradual addition of methyl iodide (62 µl, 1 eq). Later, additional sodium hydroxide solution (340 µl, 0.4 M) and methyl iodide (62 µl) were added and the solution was stirred for 2 h at room temperature. A new spot on TLC (8:2 $CHCl_3$:MeOH) at $R_f$=0.53, indicated the quantitative formation of product 16. The solution was freeze-dried and the crude residue was purified on a silica-gel column (elution with $CHCl_3$:MeOH 95:5). Product 16 was obtained in 84% yield (264.2 mg) as lightly yellow solid.

(xi) Synthesis of $N^2$,N3-etheno-6-methylthio-purine riboside, 17

5-(2-amino-6-(methylthio)-9H-purine-9-yl)-tetrahydro-2-(hydroxymethyl)furan-3,4-diol As depicted in Scheme 4, step c, 1.3 M bromoacetaldehyde (0.78 ml, 6 eq) was added to 6-methylthio-2-amino-purine riboside (53 mg, 0.17 mmol) in EtOH (10 ml). The pH of the reaction was adjusted to 4.5 throughout the entire reaction time by the drop-wise addition of 1 M $NH_4HCO_3$ (aq) and 10% HCl solutions. The reaction mixture was stirred at 38° C. for 48 h. TLC (8:2 $CHCl_3$:MeOH) showed a new spot, $R_f$=0.51. A few drops of saturated sodium bicarbonate aqueous solution were added to neutralize the mixture (pH 8). The mixture was then diluted by water (100 ml) and freeze-dried. Finally, the residue was purified on a silica-gel column and eluted with $CHCl_3$:MeOH 85%:15%. Product 17 was obtained in 33% yield (18.3 mg) as lightly yellow solid, mp 171-178° C. $^1$H NMR (300 MHz, $CD_3OD$): 8.62 (s, H-8); 7.82 (etheno); 7.71 (etheno); 6.01 (d, 1H, H-1'); 4.79 (t, 1H, H-2'); 4.41 (t, 1H, H-3'); 4.16 (m, 1H, H-4'); 3.89 (dd, 1H, H-5'); 3.85 (dd, 1H, H-5'); 3.26 (s, $CH_3$) ppm. MS m/z: 338 ($MH^+$).

(xii) Synthesis of N1,N²-etheno-6-methylthio-purine riboside

Tetrahydro-2-(hydroxymethyl)-5-(9-(methylthio)-3H-imidazo[1,2-f]furan-3-ol

This product was obtained following the same conditions as for product 17, starting from 0.56 mmol 16. pH of the reaction was adjusted to 6.4 throughout the entire reaction time. TLC (8:2 CHCl$_3$:MeOH) showed a new spot, R$_f$=0.37 (end product). The reaction residue was purified on a silica-gel column and eluted with CHCl$_3$:MeOH 92:8. The end product was obtained in 47% yield (83.7 mg) as a light yellow solid, in addition to 17 (15% yield, 24 mg). $^1$H NMR (300 MHz, CD$_3$OD): 8.49 (s, 1H), 8.17 (Abq, 1H), 7.83 (Abq, 1H), 6.33 (d, 1H, J=5.1 Hz), 4.67 (t, 1H, J=4.8, 5.1 Hz), 4.43 (t, 1H, J=4.5, 4.8 Hz), 4.28 (m, 1H, J=3.0, 3.6 4.5 Hz), 3.86 (dd, 1H, J=3.0, 12.3 Hz), 3.82 (dd, 1H, J=3.6, 12.3 Hz), 3.35 (s, 3H) ppm. MS m/z: 338 (MH$^+$).

(xiii) General Procedure for the Reaction of 2-amino-6-chloropurine riboside 12 With Aromatic Amines for the Preparation of 13a-d Aromatic amine analogue (6 eq) was added to a solution of the 2-amino-6-chloropurine riboside, 12 (0.33 mmol) in EtOH (10 ml). The reaction mixture was heated at 100° C. for 18 h. TLC (CHCl$_3$:MeOH, 9:1) indicated that the reaction was completed. The mixture was concentrated under reduced pressure. The crude products were purified by flash column chromatography on silica gel using 90% CHCl$_3$/MeOH as the solvent system. Yields: 13c, 92% (112.9 mg), 13b, 91% (167.8 mg), 13a, 91% (130.0 mg), 13d, 90% (137.5 mg).

(xiv) 2-Amino-N⁶-benzyl-purineriboside, 13c

5-(2-amino-6-(N-benzyl)-9H-purine-9-yl)-tetrahydro-2-(hydroxymethyl)furan-3,4-ol:

$^1$H NMR (600 MHz, CDCl$_3$): 7.39 (s, 1H, H-8); 7.29 (m, 5H, benzyl); 5.66 (d, 1H, H-1', J=9 Hz); 5.09 (s, 2H, CH$_2$); 4.86 (t, 1H, H-2', J=9, 18 Hz); 4.30 (m, 1H, H-3'); 3.79 (m, 1H, H-4'); 3.64-3.57 (m, 2H, H-5') ppm. MS m/z: 372 (MH$^+$). HRMS calcd for C$_{17}$H$_{21}$N$_6$O$_4$ 373.3866 found 373.1624.

(xv) 2',3',5'-Tri-O-acetylated-2-amino-N⁶-(2,3-dimethoxybenzyl)-purine riboside, 13b

5-(2-amino)-6-(2,3-dimethoxybenzyl)-9H-purin-9-yl)-tetrahydro-2,3,5-(tri-O-acetate)furan $^1$H NMR (200 MHz, CD$_3$OD): 7.86 (s, 1H, H-8); 7.57 (m, 2H, benzyl); 7.30 (s, 1H, benzyl); 6.41 (d, 1H, H-1', J=5.0 Hz); 5.98 (t, 1H, H-2', J=5.0, 5.6 Hz); 5.84 (t, 1H, H-3', J=5.1, 5.6 Hz); 5.27 (s, CH$_2$); 4.36 (m, 2H, H-4', H-5'); 3.86 (s, OCH$_3$); 3.77 (s, OCH$_3$); 2.07-2.11 (9H, CH$_3$) ppm. MS m/z: HRMS calcd for C$_{25}$H$_{31}$N$_6$O$_9$ 559.5529 found 559.2147.

(xvi) 2-Amino-N⁶-2,3-dimethoxybenzyl)-purineriboside, 13a

5-(2-amino-6-(2,3-dimethoxybenzyl)-9H-purine-9-yl)-tetrahydro-2-(hydroxymethyl)furan-3,4-ol:

$^1$H NMR (300 MHz, CDCl$_3$): 7.68 (s, 1H, H-8); 7.25 (m, 3H, benzyl); 6.05 (d, 1H, H-1', J=6.6 Hz); 5.88 (s, 2H, CH$_2$); 5.36 (m, 1H, H-2'); 5.19 (m, 1H, H-3'); 4.72 (m, 1H, H-4'); 4.51 (m, 2H, H-5'), 4.18 (s, CH$_3$), 4.15 (s, CH$_3$) ppm. MS m/z: 433 (MH$^+$). HRMS calcd for C$_{19}$H$_{24}$N$_6$O$_6$ 432.4307 found 432.1757.

(xvii) 2-Amino-N⁶,N⁶-dibenzyl-purineriboside, 13d

5-(2-amino-6-(N-dibenzyl)-9H-purine-9-yl)-tetrahydro-2-(hydroxymethyl)furan-3,4-ol:

$^1$H NMR (600 MHz, CDCl$_3$): 7.83 (s, 1H, H-8); 7.39 (m, 5H, benzyl); 5.68 (d, 1H, H-1', J=7.5 Hz); 4.93 (s, 2H, CH$_2$); 4.38 (s, 2H, CH$_2$); 5.18 (m, 1H, H-2'); 4.33 (m, 1H, H-3'); 3.95 (m, 1H, H-4'); 3.87 (m, 2H, H-5') ppm. MS m/z: 463 (MH$^+$). HRMS calcd for C$_{24}$H$_{26}$N$_6$O$_4$ 462.4012 found 462.2016.

(xviii) Reaction of 6-aromatic amines-2-aminopurine riboside Derivatives 13a-d With bromoacetaldehyde to Produce N²,N3-etheno Products 14a-d Bromoacetaldehyde (6 eq) was added to a solution of 6-aromatic amine-2-aminopurine riboside (0.30 mmol) in a mixture of H$_2$O/NH$_4$HCO$_3$/HCl (6 mL), pH 4.5 and EtOH (3 mL). The reaction mixture was stirred at 38° C. for 20 h. TLC showed the disappearance of starting material, and presence of a new spot of the product Rf 0.63, 0.35, 0.36, 0.46, respectively. The mixture was evaporated in vacuo to about half-volume to remove EtOH. A few drops of saturated sodium bicarbonate aqueous solution were added to neutralize the mixture (pH 8). Then the mixture was diluted by adding water (100 mL) and freeze-dried overnight. Yields: 14a, 87% (103.6 mg), 14b, 73% (68 mg), 14c, 61% (89.1 mg), 14d, 73% (99.86 mg). mp 167-172° C., 96-101 ° C., 205-208° C., 112-115° C., respectively.

(xix) 2',3',5'-Tri-O-acetylated-N⁶-(2,3-dimethoxybenzyl)-N²,N3-etheno-purine riboside, 14b

2-(4-(2,3-dimethoxybenzyl)-1H-imidazo[2,1-e]purin-1-yl)-tetrahydro-2,3,5-(tri-O-acetate)furan:

$^1$H NMR (300 MHz, CD$_3$OD): 8.436 (s, 1H, H-8); 8.02 (d, 1H, etheno, J=3.9 Hz); 7.73 (d, 1H, etheno, J=3.9 Hz); 6.95 (m, benzyl); 6.14 (d, 1H, H-1', J=5.4 Hz); 5.67 (CH$_2$); 4.96 (s, CH$_3$), 4.80 (s, CH$_3$); 4.71 (t, 1H, H-2', J=4.8 5.4 Hz); 4.43 (t, 1H, H-3', J=4.8, 5.1 Hz); 4.17 (m, 1H, H-4' J=3.0, 3.3, 5.19 Hz); 3.88 (dd, 1H, H-5', J=3.0, 3.3, 15.3 Hz); ppm. $^{13}$C NMR (300 MHz, CD$_3$OD): 154.2 (C-6); 131.9 (C-4); 142.6 (C-2); 125.3 (C-8); 121.5 (C-5); 113.8 (etheno); 108.2 (etheno); 89.8 (C-1'); 62.8 (C-4'); 87.2 (C-2'); 75.7 (C-3'); 72.0 (C-5'); 56.3 (s, CH$_3$); 49.6 (s, CH$_3$) 44.7 (benzyl) 49.8-48.1 (m, benzyl); 129.2-128.6 (benzyl) ppm. MS m/z: HRMS calcd for C$_{27}$H$_{31}$N$_6$O$_9$ 583.5749 found 583.2147.

(xx) N⁶-benzyl-N²,N3-etheno-purineriboside, 14c

2-(4-benzyl-1H-imidazo[2,1-e]purin-1-yl)-tetrahydro-5-(hydroxymethyl)furan-3,4-diol $^1$H NMR (600 MHz, CD$_3$OD): 8.49 (s, 1H, H-8); 8.19 (Abq, 1H, etheno); 7.75 (Abq, 1H, etheno); 6.08 (d, 1H, H-1', J=2.4 Hz); 5.52 (dd, 2H, CH$_2$, J=7.5, 9 Hz 4.70 (t, 1H, H-2', J=2.4, 5.4 Hz); 4.38 (t, 1H, H-3', J=5.4, 5.7 Hz); 4.15 (m, 1H, H-4'); 3.84 (dd, 1H, H-5', J=1.5, 6 Hz); 3.76 (dd, 1H, H-5', J=1.5, 6.3 Hz) ppm. $^{13}$C-NMR (600 MHz, CD$_3$OD):

154.61 (C-6); 138.71 (C-4); 145.63 (C-2); 142.75 (C-8); 113.78 (C-5); 108.93 (etheno); 121.34 (etheno); 89.68 (C-1'); 44.30 (C-4'); 75.81 (C-2'); 71.85 (C-3'); 62.73 (C-5'); 48.49 (CH$_2$); 128.32-130.09 (benzyl) ppm. MS m/z: 397 (MH$^+$). HRMS calcd for C$_{19}$H$_{21}$N$_6$O$_4$ 397.2492 found 397.1642.

(xxi) N$^6$-dibenzyl-N$^2$,N3-etheno-purineriboside, 14d 2-(4-dibenzyl-1H-imidazo[2,1-e]purin-1-yl)-tetrahydro-5-(hydroxymethyl)furan-3,4-diol $^1$H NMR (600 MHz, CD$_3$OD): 8.46 (s, 1H, H-8); 8.09 (d, 1H, etheno); 7.63 (d, 1H, etheno); 6.27 (d, 1H, H-1', J=2.4 Hz); 4.73 (t, 1H, H-2', J=2.4, 51 Hz); 4.38 (t, 1H, H-3', J=2.4, 4.5 Hz); 4.27 (q, 1H, H-4', J=4.5, 6.0 Hz); 3.81 (dd, 1H, H-5', J=1.5, 6.3 Hz); 3.75(dd, 1H, H-5', J=1.5, 6.0 Hz) ppm. $^{13}$C-NMR (600 MHz, CD$_3$OD): 154.31 (C-6); 137.42 (C-4); 144.82 (C-2); 136.71 (C-8); 119.51 (C-5); 119.32 (etheno); 111.12 (etheno); 90.88 (C-1'); 79.43 (C-4'); 76.38 (C-2'); 71.69 (C-3'); 61.97 (C-5'); 49.85-48.15 (2×CH$_2$); 128.63-129.20 (benzyl) ppm. MS m/z: 487 (MH$^+$). HRMS calcd for C$_{26}$H$_{27}$N$_6$O$_4$ 487.53065 found 487.2094.

(xxii) N$^6$-(2,3-dimethoxybenzyl)-N$^2$,N3-etheno-purineriboside, 14a 2-(4-(2,3-dimethoxybenzyl)-1H-imidazo[2,1-e]purin-1-yl)-tetrahydro-5-(hydroxymethyl)furan-3,4-diol $^1$H NMR (300 MHz, CD$_3$OD): 8.436 (s, 1H, H-8); 8.02 (d, 1H, etheno); 7.73 (d, 1H, etheno); 6.95 (m, benzyl); 6.14 (d, 1H, H-1', J=5.5 Hz); 5.67 (s, CH$_2$); 4.96 (s, CH$_3$); 4.80 (s, CH$_3$); 4.71 (t, 1H, H-2', J=4.5, 5.5 Hz); 4.43 (t, 1H, H-3', J=4.5, 5.8 Hz); 4.17 (m, 1H, H-4 ); 3.88 (m, 2H, H-5'); ppm. $^{13}$C NMR (300 MHz, CD$_3$OD): 154.18 (C-6); 131.99 (C-4); 142.60 (C-2); 125.31 (C-8); 121.46 (C-5); 113.77 (etheno); 108.18 (etheno); 89.76 (C-1'); 62.82 (C-4'); 87.22 (C-2'); 75.75 (C-3'); 72.03 (C-5'); 56.30 (s, CH$_3$); 49.56 (s, CH$_3$) 44.71 (benzyl) 49.85-48.15 (m, benzyl); 128.63-129.20 (benzyl) ppm. MS m/z: 456 (MH$^+$). HRMS calcd for C$_{21}$H$_{24}$N$_6$O$_6$ 456.4521 found 456.1757.

(xii) Synthesis of 6-thiomethyl-purine-2'-deoxy-riboside, 21

As depicted in Scheme 6, step a, trifluoroacetic anhydride (0.72 ml, 5.04 mmol) was added to a cooled solution of 2'-deoxyguanosine, 19 (0.180 mg, 0.63 mmol) in dry pyridine (12.6 ml) in an ice bath under nitrogen atmosphere. After 40 min, a suspension of sodium thiomethoxide (1.32 g, 18.9 mmol) in anhydrous DMF was added in portions. After 24 h, the reaction mixture was poured into 70 ml of 0.16 M ammonium bicarbonate, with vigorous stirring for 1 h (Kung and Jones, 1991). A new spot on TLC (8:2 CHCl$_3$:MeOH) at R$_f$=0.59, indicated the formation of product 21. The solvent was evaporated in vacuo and the crude residue was purified on a silica-gel column (elution with CHCl$_3$:MeOH 90:10). Product 21 was obtained in 36% yield (73 mg) as a light yellow solid. $^1$H NMR (300 MHz, CD$_3$OD): 8.18 (s, H-8); 6.33 (t, 1H, H-1'); 4.59 (m, 1H, H-3'); 4.08 (m, 1H, H-4'); 3.88 (dd, 1H, H-5'); 3.78 (dd, 1H, H-5'); 2.81 (m, 1H, H-2'); 2.37 (m, 1H, H-2'); 2.63 (s, CH$_3$) ppm. MS m/z: 298 (MH$^+$) HRMS calcd for C$_{11}$H$_{15}$N$_5$O$_3$S 297.181 found 297.0896. mp 128-132° C.

Alternatively, as depicted in step b, 6-thioguanosine, 20, (1 g, 3.53 mmol) was treated with 0.4 M sodium hydroxide and methyl iodide, as described before for 6-thioinosine (Jack et al., 1958). A new spot on TLC (8:2 CHCl$_3$:MeOH) at R$_f$=0.59, indicated the quantitative formation of product 21. The solid was collected by filtration. Product 21 was obtained in 85% yield (954 mg) as a white solid.

(xiii) Synthesis of 6-thiomethyl-N$^2$,N3-etheno-purine-2'-deoxy-riboside, 22

As depicted in Scheme 6, step c, 1.3 M bromoacetaldehyde solution (0.83 ml, 6 eq) was added to a solution of 6-thiomethyl-purine-2'-deoxy-riboside 21 (57 mg, 0.18 mmol) in NH$_4$HCO$_3$/HCl buffer (6 ml), pH 4.8, and EtOH (1 ml). The reaction mixture was stirred at room temperature for 8 h (Kusmierek et al., 1989). The mixture was evaporated in vacuo to about half-volume, and EtOH was removed. A few drops of 1 M sodium hydrogencarbonate aqueous solution were added till pH 8 was attained. The mixture was diluted by water (100 ml) and freeze-dried. The product was purified on silica-gel column and eluted with (MeOH:CH$_2$Cl$_2$) (11:89). Product 22 was obtained as a light yellow solid in 48% yield (52 mg). $^1$H NMR (300 MHz, D$_2$O): 8.59 (s, 1H, H-8); 7.79 (d, 1H, etheno); 7.70 (d, 1H, etheno); 6.34 (t, 1H, H-1'); 4.62 (m, 1H, H-3'); 4.04 (m, 1H, H-4'); 3.78 (m, 2H, H-5'); 3.26 (s, CH$_3$); 2.87 (m, 1H, H-2'); 2.50 (m, 1H, H-2') ppm. $^{13}$C NMR (300 MHz, CD$_3$OD): 149.75 (C-6); 148.15 (C-4); 140.76 (C-2); 147.49 (C-8); 128.72 (C-5); 134.03 (etheno); 109.82 (etheno); 89.24 (C-1'); 72.58 (C-4'); 40.83 (C-2'); 85.83 (C-3'); 63.25 (C-5'); 16.76 (CH$_3$) ppm. MS m/z: 322 (MH$^+$) HMRS calcd for C$_{13}$H$_{15}$N$_5$O$_3$S 321.142 found 321.0896. mp 130-134° C.

(xiv) Synthesis of 6-thiomethyl-N1,N$^2$-etheno-2'-deoxy-adenosine, 24

As depicted in Scheme 7, step a, 1.3 M bromoacetaldehyde solution (1.13 ml, 6 eq) was added to a solution of 6-thiomethyl-2'-deoxyguanosine 21 (73 mg, 0.24 mmol) in NH$_4$HCO$_3$/HCl buffer (8 ml), pH 4.8, and EtOH (1.5 ml). The reaction mixture was stirred at room-temperature for 8 h. The mixture was evaporated in vacuo to about half-volume, and EtOH was removed. A few drops of 1 M sodium hydrogencarbonate aqueous solution were added to neutralize the mixture (pH 8). The mixture was diluted by water (100 ml) and freeze-dried. The product was purified on silica-gel column and eluted with (MeOH:CH$_2$Cl$_2$) (11:89). Rf=0.10. Product 24 was obtained as a light yellow solid in 27% yield (21 mg). $^1$H NMR (300 MHz, D$_2$O): 8.34 (s, 1H, H-8); 8.10 (d, 1H, etheno); 7.79 (d, 1H, etheno); 6.67 (t, 1H, H-1'); 4.47 (m, 1H, H-3'); 4.23 (m, 1H, H-4'); 4.06 (m, 2H, H-5'); 3.32 (s, CH$_3$); 2.89 (m, 1H, H-2'); 2.61 (m, 1H, H-2') ppm. MS m/z: 322 (MH$^+$).

(xv) Synthesis of N1,N$^2$-etheno-2'-deoxy-adenosine, 25

As depicted in Scheme 7, step b, a mixture of products 22 and 24 (101 mg, 0.31 mmol) was dissolved in 2 M NH$_3$ solution in EtOH (15 ml) in a thick, sealed ampule. The solution was stirred at 100° C. for 24 h. A new spot on TLC (CHCl$_3$:MeOH) at R$_f$=0.11, indicated the formation of product 25. The solvent was evaporated to dryness in vacuo, and the residue was separated on a silica-gel column (CHCl$_3$:MeOH 1:1). Product 25 was obtained in 83% yield as a light yellow solid. $\phi_{290}$=0.07, pH 7.0 $\epsilon$(238 nm): 4.12×10$^3$, (308 nm): 1.02×10$^3$. $^1$H NMR (300 MHz, CD$_3$OD): 8.51 (s, H-8); 8.07 (etheno); 7.80 (etheno); 6.50 (t, 1H, H-1'); 4.61 (m, 1H, H-3'); 4.06 (m, 1H, H-4'); 3.81 (m, 2H, H-5'); 3.10 (m, 1H, H-2'); 2.52 (m, 1H, H-2') ppm. $^{13}$C NMR (300 MHz, CD$_3$OD): 144.96 (C-6); 145.52 (C-4); 151.05 (C-2); 143.51 (C-8); 144.96 (C-5); 121.40 (etheno); 108.57 (etheno); 89.42 (C-1'); 72.57 (C-4'); 41.19 (C-2'); 85.90 (C-3'); 63.17 (C-5') ppm. MS m/z: 290 (MH$^+$).

Example 1

Synthesis of N$^2$,N3-etheno-adenosine (Tetrahydro-2-(hydroxyl-methyl)-5-(4-(amino)-1H-imidazo[2,1-e]purin-1-yl)furan-3,4-diol; N$^2$,N3-ε-A; Compound 4)

Compound 4 was obtained as described hereinabove and depicted in Schemes 1-4.

As depicted in Scheme 1, compound 4 was obtained from 6-chloro-2-amino-purine riboside, 6. In the last step, step d, N$^2$,N3-etheno-2',3',5'-tri-O-acetyl-6-chloro-purine riboside, 8, (25 mg, 0.055 mmol) was dissolved in 2 M NH$_3$ solution in EtOH (10 ml) in a thick sealed ampoule. The solution was stirred at 100° C. for 24 h, then at room temperature overnight. A new spot on TLC (MeOH) at R$_f$=0.63, indicated the formation of product 4. The solvent was evaporated to dryness in vacuo, and the residue was separated on a silica-gel column (CHCl$_3$:MeOH 1:1). Product 4 was obtained in 43% yield as a light yellow solid. $^1$H NMR (300 MHz, CD$_3$OD): 8.37 (s, H-8); 7.78 (etheno); 7.26 (etheno); 6.25 (d, 1H, H-1'); 4.63 (t, 1H, H-2'); 4.38 (t, 1H, H-3'); 4.25 (m, 1H, H-4'); 3.85 (dd, 1H, H-5'); 3.82 (dd, 1H, H-5') ppm. MS m/z: 307 (MH$^+$).

As depicted in Scheme 2, compound 4 was obtained from the same starting material, 6, by a two-phase synthesis, in 12% yield.

In order to improve the overall yield of the final product, and as depicted in Scheme 4, we attempted an alternative synthetic approach starting from 6-methylthio-2-amino-purine riboside, 16, for both directing the ring cyclization at N$^2$,N3-positions, and enabling eventually facile substitution of C6 by amine. Compound 16 was prepared by treating 6 with NaSMe in DMSO at 60° C. for 40 h (Secrist et al., 1994). Alternatively, 16 was obtained in 84% yield by methylation of thioguanosine, 15 (Jack et al., 1958). Bromoacetaldehyde solution was added to 6-methylthio-2-amino purine riboside 16 in EtOH/water, at pH 4.5, 38° C. for 48 h, to provide in good yield and absolute regiospecificity, the etheno product 17. Finally, product 17 was treated with ethanolic ammonia at 150° C. for 12 h to provide product 4 in 33% yield. Thus, as depicted in step d, N$^2$,N3-etheno-6-methylthio-purine riboside, 17, (10.4 mg, 0.03 mmol) was dissolved in 2 M NH$_3$ solution in EtOH (10 ml) in a thick sealed ampoule. The solution was stirred at 150° C. for 6 h and then another 24 h at 100° C. A new spot on TLC (8:2 CHCl$_3$:MeOH) at R$_f$=0.40, indicated the formation of product 4. The solvent was evaporated to dryness in vacuo and the crude residue was purified on a silica-gel column (elution with CHCl$_3$:MeOH 1:1). Product 4 was obtained in 33% yield (3.1 mg) as a lightly yellow solid.

Example 2

Characterization of N$^2$,N3-ε-A (Compound 4) and of N$^2$,N3-ε-2-deoxy-A (Compound 23)

2(i) Regiochemistry of the Ring Cyclization Reaction of Compound 4

To assign the regiochemistry of the ring closure reaction as either 4 or 18 (linear N1,N$^2$-ε-A), we measured $^1$H-$^1$H-2D-NOESY spectra of intermediate ε-products 8, 14a and 17. A clear cross peak between the etheno H5 and the ribose H1' proved the angular geometry of these products. A cross peak between H2 and H2' indicated the anti-geometry of the products (not shown).

2(ii) Mechanism and Regiochemistry Control of the Cyclization Reaction

Leonard et al. noticed that the treatment of guanosine with chloroacetaldehyde at pH 4.5 resulted in no product. However, at elevated pH (pH 6.5), the linear N1,N$^2$-ε-G product, 5 was formed. To control the regiochemistry of this reaction, Leonard selected O$^6$-benzylguanine to direct the reaction with chloracetaldehyde to guanosine N$^2$ and N3 positions by hindering sterically N1 (Sattsangi et al., 1977).

Singer et al. reacted 5'-phosphate-O$^6$-benzyl-2'-deoxyguanosine (Kusmierek et al., 1989), with chloroacetaldehyde at pH ~8. 2'-Deoxy-N$^2$,N3-ε-G, 3, was obtained in 18% yield, accompanied by several by-products. The linear nucleotide 2'-deoxy-N1,N$^2$-ε-G, 5, was obtained in 55% yield at basic pH (Kusmierek and Singer, 1992).

In our ring closure reactions of various purine-riboside derivatives with bromoacetaldehyde at pH 4.5 (Schemes 1-4), we observed that the nature of C6-substituent, either Cl, NHCH$_2$Ar, or SMe (as in 12, 13, and 16, respectively), plays no role in directing the ring closure. All these reactions occurred with complete regiospecificity, forming only the N$^2$,N3-ε-purine riboside analogue.

Based on our observations, and those of others, we suggest that the regiospecificity of the reaction is controlled by pH, rather than by steric or electronic characteristics of the purine reactant. Specifically, at pH 4.5 the N1-position of analogues 13 and 16, which is the most basic position in this ring system, is protonated and is not available for nucleophilic attack, thus making the N3-nitrogen the favored nucleophilic-site. For the chloro analogue, 12, probably no N1-protonation occurs at pH 4.5 due to the most significant electron-withdrawing effect of the adjacent chloro group. However, the chloro substituent reduces also the nucleophilicity of N1. That is, N3-nitrogen is the preferred nucleophilic site also in analogue 12.

Indeed, when we repeated the reaction of 16 with bromoacetaldehyde at pH 6.4, the major product was N1,N$^2$-ε-6-SMe-purine riboside, (47% yield), accompanied by some 17 (15% yield). At an elevated pH, N1 in 16 is not protonated. Furthermore, electron donations of two electron-rich substituents ortho to N1 result in higher electron density at N1, as compared to N3. Therefore, at pH 6.4 the major product is the N1,N$^2$-ε-analogue.

The mechanism of ring cyclization to form etheno products 8, 14, and 17 involves, first, the displacement of the bromoacetaldehyde bromide by the pyrimidine N3 nitrogen, rather than the exocyclic nitrogen (Scheme 5). This step in the mechanism is supported by literature data on the reaction of 2-aminopyridines with α-haloketones (Hand and Paudler, 1982). The cyclic nitrogen is the favored nucleophilic site in 2-aminopyridine, since the positive charge that develops in the transition state is stabilized by resonance interaction with the exocyclic amine, as shown by Hand and Paudler. The displacement of bromide by the pyrimidine N1 nitrogen (at pH 4.5) is impossible, as mentioned above.

In the second step, the N$^2$-exocyclic amine in 12, 13, and 16 reacts with the aldehyde moiety (Beland et al., 1984), followed by elimination of a water molecule.

2(iii) Spectral Properties of Compounds 4 and 23

Absorption spectra of compounds 4 and 23 were measured using a Varian array-1E UV-Visible spectrometer. Spectra were determined in dilute HCl or NaOH solutions in the pH range of 1.6-12.3 or at pH 7.0. The concentration of the samples of 4 in aqueous solutions and in organic solvents was of the order of $4.85 \times 10^{-5}$ M and of 23 in aqueous solutions was of the order of $5.04 \times 10^{-5}$ M.

Emission spectra of compounds 4 and 23 were measured using an Aminco-Bowman series 2 Luminescence Spectrometer. Measurement conditions included: 740-750 V sensitivity, and a 4 or 2 nm slit in the emission spectra for aqueous or organic solutions, respectively. Emission spectra were corrected by the subtraction of the medium's emission spectrum. Spectra were determined in dilute HCl or NaOH solutions in the pH range of 1.6-12.3 or at pH 7. The concentration of the samples of 4 was of the order of $4.85 \times 10^{-5}$ M for aqueous and organic solutions and of 23 in the order of $5.04 \times 10^{-5}$ M for aqueous solutions. All organic solvents were freshly distilled prior to emission measurements. Measurements of the emission of the nucleoside analogue were conducted with subtraction of the solvent's emission. The quantum yield of each compound was calculated from the observed absorbance at 290 nm and the area of the fluorescence emission band. Quinine sulfate was used as reference compound assuming a quantum yield value of 0.55 (Andrew et al., 1988).

The absorption spectrum of compound 4 in water shows two bands, at 234 nm ($12.6 \times 10^3$) and 274 nm ($3.3 \times 10^3$) (FIG. 1). The absorption of 4 at pH 12.3 is almost identical to that at neutral pH (Table 1). However, at pH 1.6, there is a blue shift, due to protonation of 4. Upon excitation of 4 in water at 290 nm, maximum emission is observed at 420 nm (quantum yield is 0.03). This value represents a red shift of emission maximum as compared to $N^2,N3$-$\epsilon$-G (maximum emission 410 nm, excitation at 280 nm) (Sattsangi et al., 1977). At basic pH, the emission spectrum of 4 is identical to that at pH 7 (Table 2). However, at acidic pH, a blue-shift and reduced quantum yield are observed.

In organic solvents, the emission spectrum of 4 is linearly dependent on the polarity of the medium (Table 3). Thus, increase of the solvent polarity from diozane ($\epsilon_d$ 2.2) to DMSO ($\epsilon_d$ 47.6), resulted in increase of both $\lambda_{max}$ (from 434 to 458 nm) and of $\phi$ (from 0.042 to 0.085). This polarity-dependence of 4 is very different from that of the related $N^2,N3$-$\epsilon$-G. The wavelength of emission maxima of the latter does not change significantly with decreasing solvent polarity. On the other hand, quantum yields show substantial increase with decreasing solvent polarity (Sattsangi et al., 1977).

TABLE 1

Absorption data for compound 4 at $4.85 \times 10^{-5}$ M at several pH values

| PH | λmax | $\epsilon d \times 10^3$ |
|---|---|---|
| 1.6 | 224 | 6.17 |
|  | 268 | 14.22 |
| 7.0 | 234 | 12.58 |
|  | 274 | 3.31 |
| 12.3 | 234 | 13.89 |
|  | 276 | 3.69 |

TABLE 2

Emission data for compound 4 at $4.85 \times 10^{-5}$ M at several pH values

| PH | λmax | φ |
|---|---|---|
| 1.6 | 396 | 0.021 |
| 7.0 | 420 | 0.032 |
| 12.3 | 420 | 0.031 |

TABLE 3

Emission data for 4 at $4.85 \times 10^{-5}$ M in various organic solvents

| Solvent | $\epsilon d$ | φ | λmax |
|---|---|---|---|
| DMSO | 47.6 | 0.085 | 458 |
| DMF | 37.6 | 0.082 | 448 |
| Dioxane | 2.2 | 0.042 | 434 |

2(iv) Tautomeric and Acid-Base Equilibria of $N^2,N3$-$\epsilon$-A Nucleosides $N^2,N3$-$\epsilon$-A may exist as several tautomeric forms. These forms involve the amino tautomer and the syn/anti isomers of the NH-8 or NH-7 imino tautomers. The identification of the predominant tautomer of $N^2,N3$-$\epsilon$-A is of major importance for the evaluation of the potential of this probe, as each of the tautomers has its own H-bonding pattern. However, it is only the amino tautomer that forms the adenine H-bonding pattern with the complementary nucleobase.

$^{15}$N NMR of $N^2,N3$-$\epsilon$-A showed a sharp singlet at −309 ppm, typical of exocyclic amine, thus indicating that the predominant form is the amino tautomer. Thus, the $N^2,N3$-etheno bridge has not changed the tautomeric preferences as compared to the natural parent compound adenosine. $N^2,N3$-$\epsilon$-A, 4, is most probably neutral at physiological pH. Namely, compound 4 is expected to conserve the typical adenine H-bonding pattern.

2(v) Site of Protonation

Leonard proposed that N7 is the first site of protonation in $N^2,N3$-$\epsilon$-G, 3 (Sattsangi et al., 1977). Later, Chattopadhyaya et al. confirmed that for $N^2,N3$-$\epsilon$-G, the site of protonation is N7 of the second imidazole ring, while the imidazole ring of the parent guanine moiety is more electron deficient (Glemarec et al., 1991). For $N^2,N3$-$\epsilon$-G p$K_a$ is 2.11, while for $O^6$-benzyl-$\epsilon$-G p$K_a$ is 5.20 (Glemarec et al., 1991). The p$K_a$ of neutral $N^2,N3$-$\epsilon$-G is about one log unit lower than that of the parent compound, guanosine, which is known to bear the labile proton at N1 (corresponding to N8 in $N^2,N3$-$\epsilon$-G). The acidity difference of this magnitude may be attributed to electron withdrawal by the neighboring etheno group (Glemarec et al., 1991). Based on these observations, N7 in $N^2,N3$-$\epsilon$-A, 4, is expected to be neutral at physiological pH.

H-bonding pattern of $N^2,N3$-$\epsilon$-A is dependent not only on tautomeric equilibria, but also on acid-base equilibria, namely, on protonation states. For analyzing the protonation state of $N^2,N3$-$\epsilon$-A at physiological pH, we determined the p$K_a$ values of this system.

Specifically, we monitored the pH-titration of $N^2,N3$-E-A, 4, by fluorescence spectroscopy. $1 \times 10^{-5}$ M solutions of $N^2,N3$-$\epsilon$-A-5'-mono-phosphate were titrated by HCl in the pH range of 1.5-7.0. Three inflection points of the fitted sigmoidal graphs provided the three p$K_a$ values of this ring system: 1.92±0.08; 3.16±0.24; and 6.09±0.16.

These $pK_a$ values are attributed to three basic nitrogen atoms in $N^2,N3$-ε-A. The least basic of these atoms ($pK_a$ 1.92) is assigned to the exocyclic amine. This $pK_a$ value is lower than that of aniline ($pK_a$ 4), due to more significant delocalization of the nitrogen lone pair in the former case. The second $pK_a$ value (3.16) is attributed to the N8, corresponding to the N1 in adenosine ($pK_a$ 4). The most basic nitrogen atom in the $N^2,N3$-ε-A system is the N7 ($pK_a$ 6.09), which is in agreement with the related $N^2,N3$-ε-G ($pK_a$ of N7 is 5.20). This $pK_a$ value indicates that at physiological pH (7.4), 96% of $N^2,N3$-ε-A is non-protonated, namely, may have the same H-bonding pattern as that of the parent adenine compound.

2(vi) Base-pairing of Compound 4 with Nucleobases

Based on the above findings regarding tautomeric and acid-base equilibria of $N^2,N3$-ε-A, we expected this system to undergo base-pairing similar to that of adenine nucleos(t)ides. In order to prove that, we measured IR spectra of mixtures of $N^2,N3$-ε-A-5'-monophosphate ($N^2,N3$-ε-A-MP)/UMP and $N^2,N3$-ε-A-MP/CMP, and compared these spectra to the calculated sum of $N^2,N3$-ε-A-MP and UMP or CMP spectra. In addition, we compared the measured spectra of $N^2,N3$-ε-A-MP/UMP and $N^2,N3$-ε-A-MP/CMP mixtures to those of AMP/UMP and AMP/CMP mixtures. In order to obtain biologically relevant data, we performed IR measurements in $D_2O$ solutions, since unlike $H_2O$ explored in this study, $D_2O$ is transparent in the double bond region. Specifically, each nucleotide and nucleotide mixture were freeze-dried from $D_2O$ three times prior to dissolution in $D_2O$ and FTIR measurements (results not shown).

In these measurements we focused on the frequencies range of 1500-1800 $cm^{-1}$, corresponding to double bond and carbonyl stretches. The measured IR spectra for a 1:1 mixture of A and C was identical to the calculated sum of A and C separate spectra, namely, no specific H-bonds were formed between A and C. However, in a 1:1 mixture of A and U, a 7 $cm^{-1}$ shift to higher frequencies was observed, as compared to the calculated sum of A and U spectra, indicating the formation of H-bonds.

When the IR spectra of analogue $N^2,N3$-ε-A-MP mixture with U was compared to the calculated sum of $N^2,N3$-ε-A-MP and U spectra, a shift to higher frequencies (6 $cm^{-1}$) was observed, as for A-U, namely, $N^2,N3$-ε-A-MP H-pairs with U the same way as the parent compound does.

A and U may pair via H-bonding in solution in four different ways: AU Watson-Crick pairing; AU reverse Watson-Crick pairing; AU Hoogsteen pairing; and AU reverse Hoogsteen pairing. The above IR data indicate the involvement of the carbonyl of U in H-bonding with $N^2,N3$-ε-A-MP, yet, does not enable to differentiate between the base-pairing modes.

An IR spectrum of $N^2,N3$-ε-A-MP/CMP presented a shift to lower frequencies (7 $cm^{-1}$) as compared to the calculated sum of $N^2,N3$-ε-A-MP and CMP spectra. Cytidine forms intermolecular H-bonding, involving C2 carbonyl and N4-amine. However, upon the addition of $N^2,N3$-ε-A-MP C2 carbonyl is not involved anymore in H-bonding (as in AC reverse Hoogsteen), and shifts to lower frequencies.

IR spectra of all compounds were measured using an FT/IR-4200 (Fourier Transform Infrared Spectrometer)—JASCO. The nucleotides were lyophilized from $D_2O$ before being dissolved again in $D_2O$ for spectroscopic measurement for three times. The nucleotides complexes were prepared simply by mixing the solutions of each other in the same concentration of 20 mM and ionic strength of 0.1 M NaCl. We have used primarily fixed thickness cells with $CaF_2$ windows.

2(vii) Fluorescence Life-Time of $N^2,N3$-ε-A Analogues

Fluorescent emission is a random process, and the excited molecules emit photons within a certain time, usually of the order of ns. For $N^2,N3$-ε-A, 4, and $N^2,N3$-ε-2'-deoxy-A, 23, fluorescence life times of 2.26 and 2.1 ns, respectively, were measured. These life times are relatively long, and are therefore more convenient for the fluorescence measurements.

Example 3

Spectral Properties of $N^2,N3$-ε-6-methylthio-purine riboside, 17

Among the etheno-intermediates 8, 14a, and 17, the latter analogue exhibited promising spectral properties.

Figure 3:
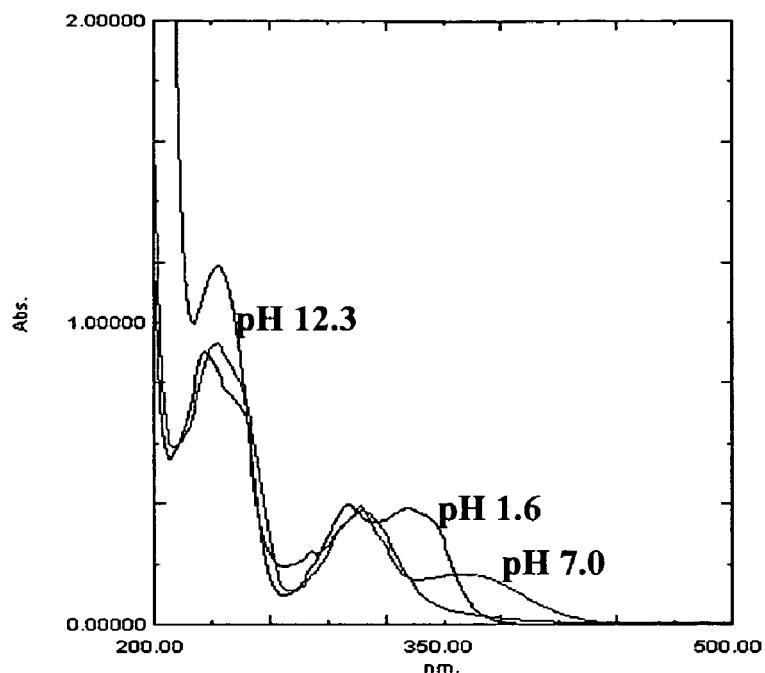
FIG. 3 shows the absorption spectra of N²,N3-etheno-6-methylthio-purine riboside (compound 17) at 4.85×10⁻⁵ M at several pH values (1.6, 7.0 and 12.3).

The absorption spectrum of compound 17 in water shows four bands at 227, 247, 307, and 345 nm (Table 4) The absorption of 17 at pH 12.3 is similar to that at a natural pH (FIG. 3). However, at pH 1.6, there is a blue shift of the absorption spectrum, due to protonation of 17.

Figure 4:
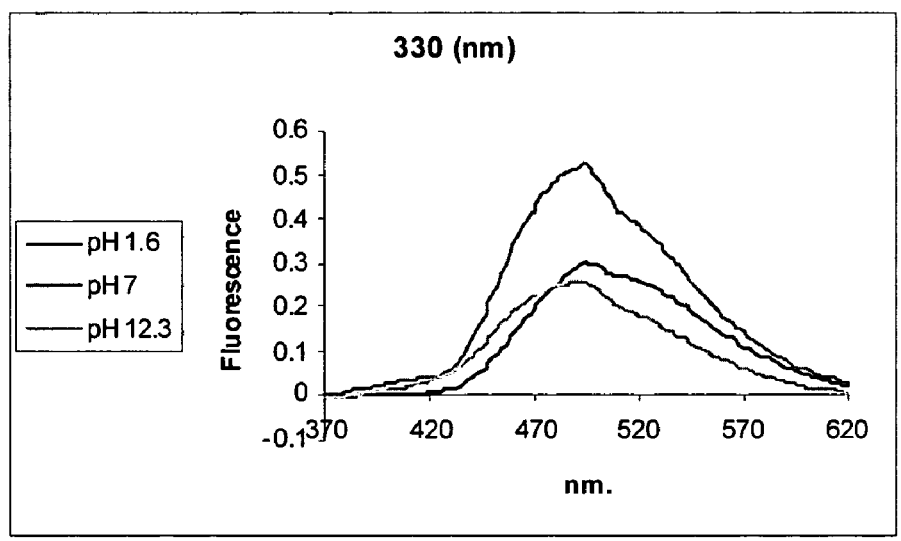
FIG. 4 shows the emission spectra of N²,N3-etheno-6-methylthio-purine riboside (compound 17) at 5.04×10⁻⁵ M at several pH values (1.6, 7.0 and 12.3).
Figure 5A:
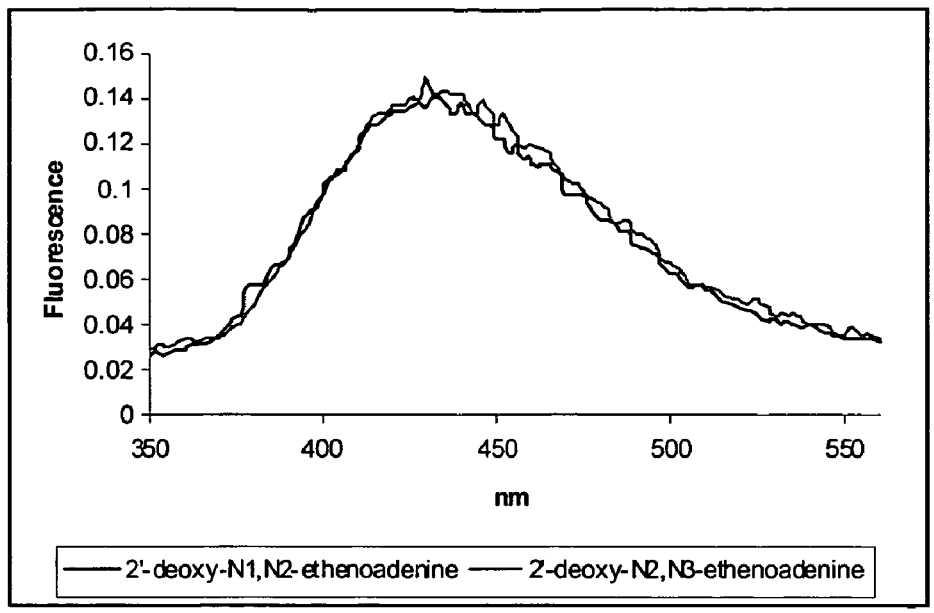
FIGS. 5A-5B show the fluorescence (A) and absorption (B) spectra of N²,N3-etheno-2'-deoxy-adenosine (compound 23), and N1,N²-etheno-2'-deoxy-adenosine.
Figure 5B:
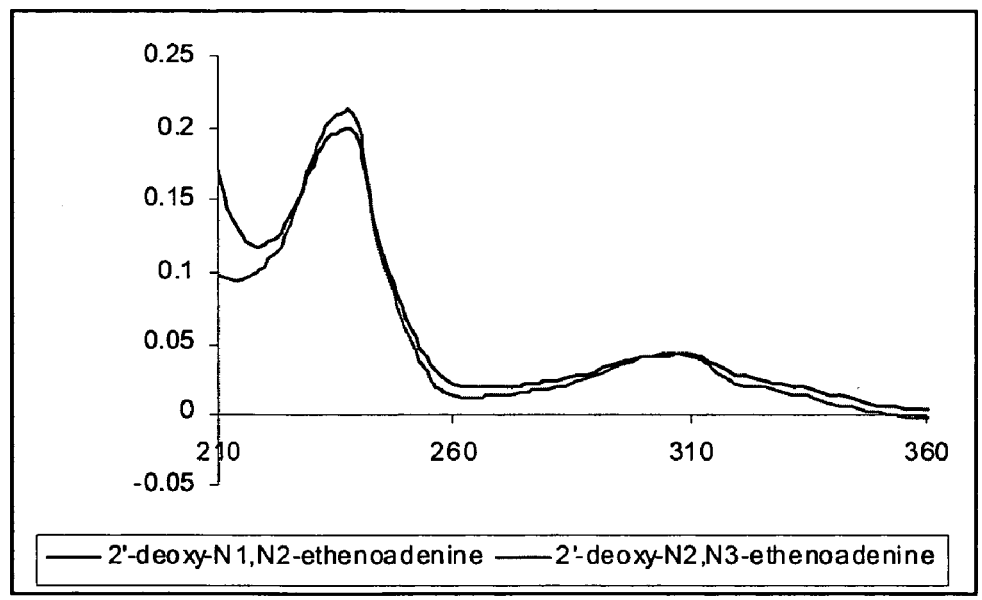

Upon excitation of 17 in water at 330 nm, maximum emission is observed at 520 nm (quantum yield is 0.15) (FIG. 4). At both acidic and basic pH (1.6, and 12.3), a blue shift and reduced yield are observed (Table 5).

TABLE 4

Absorption data for compound 17 at $5.04 \times 10^{-5}$ M at several pH values

| pH | λmax | εd × $10^3$ |
|---|---|---|
| 1.6 | 227 | 16.52 |
|  | 243 | 13.57 |
|  | 301 | 7.39 |
|  | 331 | 7.13 |
| 7.0 | 231 | 16.09 |
|  | 247 | 13.25 |
|  | 307 | 7.07 |
|  | 345 | 2.90 |
| 12.3 | 233 | 19.29 |
|  | 307 | 5.95 |

TABLE 5

Emission data for compound 17 at $5.04 \times 10^{-5}$ M at several pH values

| pH | λmax | φ |
|---|---|---|
| 1.6 | 492 | 0.037 |
|  | 516 |  |
| 7.0 | 494 | 0.152 |
|  | 518 |  |
| 12.3 | 494 | 0.067 |
|  | 520 |  |

Example 4

Synthesis of $N^2,N3$-etheno-2'-deoxyadenosine (Compound 23)

As depicted in Scheme 6, step d, product 22 (43 mg, 0.13 mmol) was dissolved in 2 M $NH_3$ solution in EtOH (15 ml) in a thick, sealed ampule. The solution was stirred at 100° C. for 24 h. A new spot on TLC ($CHCl_3$:MeOH) at $R_f$=0.11, indicated the formation of product 23. The solvent was evaporated to dryness in vacuo, and the residue was separated on a silica-gel column ($CHCl_3$:MeOH 1:1). Product 23 was obtained in 46% yield (17.3 mg) as a light yellow solid. $\phi_{290}$=0.085, pH 7.0ϵ (238 nm): 4.67×10$^3$, (308 nm): 1.23× 10$^3$. $^1$H NMR (300 MHz, CD$_3$OD): 8.35 (s, H-8); 7.88 (etheno); 7.66 (etheno); 6.46 (t, 1H, H-1'); 4.60 (m, 1H, H-3'); 4.06 (m, 1H, H-4'); 3.84 (dd, 1H, H-5'); 3.77 (dd, 1H, H-5'); 2.81 (m, 1H, H-2'); 2.45 (m, 1H, H-2') ppm. $^{13}$C NMR (300 MHz, CD$_3$OD): 150.89 (C-6); 144.42 (C-4); 147.36 (C-2); 143.15 (C-8); 107.54 (C-5); 125.55 (etheno); 113.10 (etheno); 89.46 (C-1'); 72.89 (C-4'); 41.10 (C-2'); 85.99 (C-3'); 63.28 (C-5') ppm. MS m/z: 290 (MH$^+$) HRMS calcd for C$_{12}$H$_{15}$N$_6$O$_3$ 291.2431 found 291.1206.

Example 5

General Procedure for the Preparation of Phosphorylated N$^2$,N3-etheno-nucleotides (Compounds 30a-f)

All phosphorylation reactions were carried out in flame-dried, argon-flushed, two-necked flacks sealed with rubber septa. Nucleosides were dried in vacuo for 2 days. Proton sponge was kept in a desiccator. Phosphorus oxychloride was distilled and kept under N$_2$. Tri-n-butylammonium pyrophosphate solution was prepared as described before (Fischer et al., 1993).

A solution of N$^2$,N3-etheno-guanosine, 65 (0.1 g, 0.32 mmol) in dry trimethyl phosphate (1.0 mL) was cooled to 0° C., then proton sponge (0.140 g, 2 eq) was added. After 20 min, phosphorus oxychloride (91 µL, 3 eq) was added dropwise. Stirring continued for 2 h at 0° C. TLC on a silica gel plate (1-propanol 28%/NH$_4$OH/H$_2$O 11:7:2), indicated the disappearance of starting material and the formation of a polar product (R$_f$=0.35). A mixture of Bu$_3$N (0.31 mL) and 1M (Bu$_3$NH$^+$)$_2$P$_2$O$_7$H$_2$ in DMF (2.0 ml) was added at once. After 1 min 0.2 M TEAB solution (15.45 mL) was added, and the clear solution was stirred at room temperature for 45 min. The solution was then freeze-dried overnight. The semisolid obtained after freeze-drying was chromatographed on an activated Sephadex DEAE-A25 column. The resin was washed with deionized water for 30 min and loaded with the crude reaction residue dissolved in a minimal volume of water. The separation was monitored by UV detection (ISCO, UA-6) at 280 nm. A buffer gradient of 500 ml of water to 500 ml of 0.5 M NH$_4$HCO$_3$ was applied. The relevant fractions (of the ATP and AMP derivatives) were pooled and freeze-dried three times to yield a white solid. The final purification of the products was achieved on an HPLC system (Merck-Hitachi) using a semi-preparative reverse-phase LichroCART lichrospher 60, RP-select B column (Merck, Darmstadt, Germany) and a linear gradient of acetonitrile and 0.1 M TEAA buffer (pH 7) (solvent system I) with a flow rate of 6 ml/min. These reaction conditions provided the nucleoside-triphosphate products in yields ranging from 31-63%. The corresponding nucleoside-monophosphate analogues were obtained as by-products in all reactions. Triethylammonium salts of mono- and tri-nucleotides, obtained after HPLC separation, were passed through SEPHADEX-CM C-25 and eluted with deionized water to obtain the corresponding sodium salts after freeze-drying.

The following compounds were prepared:

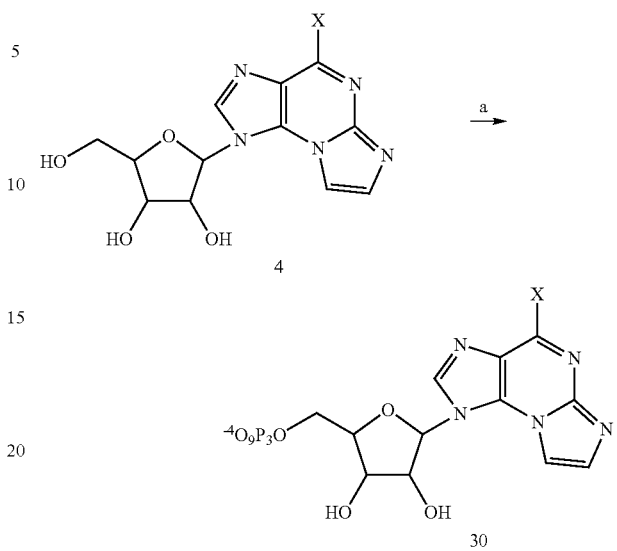

30a: Y=P$_3$O$_9^{4-}$ X=NH$_2$
30b: Y=P$_3$O$_9^{4-}$ X=SCH$_3$
30c: Y=P$_3$O$_9^{4-}$ X=O
30d: Y=P$_3$O$_9^{4-}$ X=N(H)CH$_2$(C$_6$H$_5$)
30e: Y=P$_3$O$_9^{4-}$ X=N[CH$_2$(C$_6$H$_5$)]$_2$
30f: Y=P$_3$O$_9^{4-}$ X=N(H)CH$_2$(C$_6$H$_3$)(OCH$_3$)$_2$
30a': Y=PO$_3^{2-}$ X=NH$_2$
30b': Y=PO$_3^{2-}$ X=SCH$_3$
30c': Y=PO$_3^{2-}$ X=O
30d': Y=PO$_3^{2-}$ X=N(H)CH$_2$(C$_6$H$_5$)
30e': Y=PO$_3^{2-}$ X=N[CH$_2$(C$_6$H$_5$)]$_2$
30f': Y=PO$_3^{2-}$ X=N(H)CH$_2$(C$_6$H$_3$)(OCH$_3$)$_2$ a.(1) POCl$_3$, PO(OMe)$_3$, proton sponge; (2) (Bu$_3$NH$^+$)$_2$ H$_2$P$_2$O$_7^{2-}$; (3) 0.2 M TEAB Example 6

Synthesis of N$^2$,N3-ethenoadenosine-5'-triphosphate (2-(4-(amino)-1H-imidazo[2,1-e]purin-1-yl)-3,4-dihydroxy-tetrahydro-furan-5-triphosphate; Compound 30a)

Yield 49% (24 mg). $^1$H-NMR (200 MHz, D$_2$O, pH 6) δ: 8.51 (s, 1H, H-8), 7.78 (ABq, 2H, etheno), 7.65 (ABq, 2H, Ar), 6.12 (d, 1H, H-1', J=7.5 Hz), H-2', H-3', H-4'—hidden by the water, 4.42 (m, 2H, H-5') ppm. $^{31}$P NMR (200 MHz, D$_2$O, pH 6) δ: −9.91 (d); −10.92 (d); −22.58 (t) ppm. Rt=3.41 min, solvent system I, 2:98 to 65:35, purity>95%, Rt=2.99 min, solvent system II, purity>95%. FAB (negative mode) m/z: 545 (M$^{4-}$+3H$^+$). HRFAB calcd for C$_{12}$H$_{16}$N$_6$O$_{13}$P$_3$ 544.9988 found 544.9993.

Example 7

6-SMe-N$^2$,N3-etheno-purine riboside-5'-triphosphate (2-(4-(thiomethyl)-1H-imidazo[2,1-e]purin-1-yl)-3,4-dihydroxy-tetrahydro-furan-5-triphosphate; Compound 30b)

Yield 58% (62 mg). $^1$H-NMR (200 MHz, D$_2$O, pH 6) δ: 8.90 (s, 1H, H-8), 8.01 (ABq, 2H, etheno), 7.91 (ABq, 2H, Ar), 6.18 (d, 1H, H-1', J=2.1 Hz), H-2', H-3', 4.48 (m, 1H, H-4'), 4.33 (m, 2H, H-5'), 3.12 (s, 3H, SMe) ppm. $^{31}$P NMR (200 MHz, D$_2$O, pH 6) δ: −9.85 (d); −10.85 (d); −22.32 (t); ppm. Rt=9.47 min, solvent system I, 2:98 to 65:35, purity>94%, Rt=2.72 min, solvent system II, purity>95%. FAB (negative mode) m/z: 577 (M$^{4-}$−3H$^+$).

Example 8

N$^2$,N3-ethenoguanosine-5'-triphosphate (2-(4-(oxo)-1H-imidazo[2,1-e]purin-1-yl)-3,4-dihydroxy-tetrahydro-furan-5-triphosphate; Compound 30c)

Yield 31% (19 mg). $^1$H-NMR (200 MHz, D$_2$O, pH 6) δ: 8.34 (s, 1H, H-8), 8.89 (ABq, 2H, etheno), 7.42 (ABq, 2H, Ar), 6.12 (d, 1H, H-1', J=9.0 Hz), 5.01 (t ,1H, H-2', J=7.2, 9.0 Hz), H-3', H-4'—(hidden by the water), 4.43 (m, 2H, H-5') ppm. $^{31}$P NMR (200 MHz, D$_2$O, pH 6) δ: −5.43 (d); −10.39 (d); −21.15 (t); ppm. Rt=3.71 min, solvent system I: 2:98 to 65:35, purity>95%, Rt=2.24 min, solvent system II, purity >97%. FAB (negative mode) m/z: 546 (M$^{4-}$−H$^+$). HRFAB calcd for C$_{12}$H$_{15}$N$_5$O$_{14}$P$_3$ 545.9828 found 545.9857.

Example 9

N$^6$-Benzyl-N$^2$,N3-ethenoadenosine-5'-triphosphate (2-(4-(benzyl)-1H-imidazo[2,1-e]purin-1-yl)-3,4-dihydroxy-tetrahydro-furan-5-triphosphate; Compound 30d)

Yield 63% (28 mg). $^1$H-NMR (200 MHz, D$_2$O, pH 6) δ: 8.18 (s, 1H, H-8), 7.65 (ABq, 2H, Ar), 7.32 (ABq, 2H, Ar), 6.12 (d, 1H , H-1', J=8.1 Hz), 4.72 (m, 1H, H-2'), 4.60 (m, 1H, H-3'), 4.43 (m, 1H, H-4'), 4.21 (m, 2H, H-5') ppm. $^{31}$P NMR (200 MHz, D$_2$O, pH 6) δ: −6.23 (d); −10.44 (d); −21.24 (t). ppm. Rt=4.11 min, solvent system I, 15:85 to 45:55, purity>98%, Rt=6.56 min, solvent system II, purity>95%. FAB (negative mode) m/z: 546 (M$^{4-}$−3H$^+$). HRFAB calcd for C$_{19}$H$_{22}$N$_6$O$_{13}$P$_3$ 635.33172 found 635.0463.

Example 10

N$^6$,N$^6$-Dibenzyl-N$^2$,N3-ethenoadenosine-5'-triphosphate (2-(4-(dibenzyl)-1H-imidazo[2,1-e]purin-1-yl)-3,4-dihydroxy-tetrahydro-furan-5-triphosphate; Compound 30e)

Yield 59% (33 mg). $^1$H-NMR (200 MHz, D$_2$O, pH 6) δ: 8.42 (s, 1H, H-8), 8.00 (ABq, 2H, Ar), 7.78 (ABq, 2H, Ar), 7.35 (m, 10H, benzyl), 6.30 (d, 1H, H-1', J=8.3 Hz), 5.27 (s, 4H, benzyl), H-2', H-3'—hidden by the water, 4.50 (m, 1H, H-4'), 4.25 (m, 2H, H-5') ppm. $^{31}$P NMR (200 MHz, D$_2$O, pH 6) δ: −5.37 (d); −10.67 (d); −21.27 (t); ppm. Rt=9.79 min, solvent system I, purity>99%, 25:75 to 40:60, Rt=13.44 min, solvent system II, 40:60 to 90:10, purity>95%. FAB (negative mode) m/z: 725 (M$^{4-}$+3H$^+$). HRFAB calcd for C$_{26}$H$_{28}$N$_6$O$_{13}$P$_3$ 725.3391 found 725.0932.

Example 11

N$^6$-2,3-Dimethoxybenzyl-N$^6$,N3-ethenoadenosine-5'-triphosphate (2-(4-(2,3-dimethoxybenzyl)-1H-imidazo[2,1-e]purin-1-yl)-3,4-dihydroxy-tetrahydro-furan-5-triphosphate; Compound 30f)

Yield 58% (42 mg). $^1$H-NMR (200 MHz, D$_2$O, pH 6) δ: 8.30 (s, 1H, H-8), 7.71 (ABq, 2H, Ar), 7.57 (ABq, 2H, Ar), 6.87 (m, 3H, benzyl), 6.00 (d, 1H, H-1', J=8.1 Hz), 5.24 (s, 2H, benzyl), H-2', H-3', H-4'—hidden by the water, 4.26 (m, 2H, H-5'), 3.78 (s, 3H, OCH$_3$), 3.72 (s, 3H, OCH$_3$) ppm. $^{31}$P NMR (200 MHz, D$_2$O, pH 6) δ: −6.59 (d); −10.40 (d); −21.28 (t); ppm. Rt=6.13 min, solvent system I, purity>99%, 15:85 to 45:55, Rt=11.87 min, solvent system II, purity>95%. FAB (negative mode) m/z: 695 (M$^{4-}$+3H$^+$). HRFAB calcd for C$_{21}$H$_{26}$N$_6$O$_{15}$P$_3$ 695.0668 found 695.06713.

Example 12

Synthesis of N$^2$,N3-etheno-2'-deoxy-adenosine-5'-triphosphate (Compound 26)

N$^2$,N3-etheno-2'-deoxy-adenosine, 23 (76.4 mg, 0.26 mmol), was 5'-triphosphorylated to produce the fluorescent ATP derivative N$^2$,N3-etheno-2'-deoxy-adenosine-5'-triphosphate, 26. Yield: 37% (18 mg). $^1$H-NMR (300 MHz, D$_2$O, pH 6) δ: 8.40 (s, 1H, H-8), 7.88 (ABq, 2H, etheno), 7.66 (ABq, 2H, Ar), 6.45 (t, 1H , H-1', J=6.6, 13.2 Hz), 4.58 (m, 1H, H-3'), 4.03 (m, 1H, H-4'), 3.78 (m, 2H, H-5'), 2.81 (m, 1H, H-2'), 2.44 (m, 1H, H-2') ppm. $^{31}$P NMR (200 MHz, D$_2$O, pH 6) δ: −8.22 (d); −10.67 (d); −22.29 (t) ppm. Rt=3.41 min, solvent system I, 2:98 to 65:35, purity>95%, Rt=2.99 min, solvent system II, purity>95%. FAB (negative mode) m/z: 529 (M$^{4-}$−H$^+$) HRFAB calcd for C$_{16}$H$_{15}$N$_6$O$_{12}$P$_3$ 529.0136, found 529.0044.

Example 13

Synthesis of N$^6$-dimethylaminomethylene-N$^2$,N3-etheno-2'-deoxy-adenosine (Compound 27)

As depicted in Scheme 8, step a, a solution of N$^2$,N3-etheno-2'-deoxy-adenosine, 23 (100 mg, 0.34 mmol) in dry DMF (5 ml) was shaken with five-fold excess of dimethylformamide dimethylacetal (230 μl) at room temperature overnight and the resulting clear solution was evaporated under vacuum. The residue was purified on alumina column and eluted at 6:4 chloroform:methanol. Product 27 was obtained as a white solid in 71% yield (85.2 mg), mp 203-208° C. $^1$H-NMR (300 MHz, CDCl$_3$): 9.37 (s, 1H, amidine), 8.35 (s, 1H, H8); 7.77 (Abq, 1H, etheno), 7.49 (Abq, 1H, etheno); 6.43 (t, 1H, H-1', J=6.6, 14 Hz); 4.61 (m, 1H, H-3'); 4.07 (m, 1H, H-4'); 3.80 (m, 2H, H-5'); 2.98 (m, 2H, H-2'); 2.85 (m, 2H, H-2'); 2.86 (s, 3H, CH$_3$); 2.85 (s, 3H, CH$_3$) ppm. MS (m/z): 346 (MH$^+$).

Example 14

Synthesis of 5'-O-di-(4,4'-dimethoxy)trityl-N$^6$-dimethylamino-methylene-N$^2$,N3-etheno-2'-deoxy-adenosine (Compound 28)

As depicted in Scheme 8, step b, a solution of N$^6$-amidine-N$^2$,N3-etheno-2'-deoxy-adenosine, 27 (100 mg, 0.16 mmol) and 4,4'-dimethoxytrityl (DMT) chloride (133.6 mg, 1.6 eq) in pyridine (4 ml) was allowed to stir at room temperature for 3 days and then was poured with stirring to ice water (10 ml). The oil was extracted with chloroform (3×15 ml), the extract was washed with water, dried over MgSO$_4$ and evaporated to dryness. Product 28 was obtained as a yellow solid in 42% yield of (40.8 mg), mp 116-120° C. $^1$H-NMR (300 MHz, CDCl$_3$): 9.54 (s, 1H, amidine); 8.63 (s, 1H, H8), 8.07 (Abq, 1H, etheno), 7.87 (Abq, 1H, etheno); 7.33-6.87 (m, 9H, Ar), 6.43 (m, 1H, H-1'); 4.61 (m, 1H, H-3'); 4.07 (m, 1H, H-4'); 3.80 (m, 2H, H-5'); 3.13 (m, 2H, H-2'); 2.87 (m, 2H, H-2'); 3.36 (s, 3H, CH$_3$), 3.33 (s, 3H, CH$_3$) ppm. MS (m/z): 609 (MH$^+$).

Example 15

Synthesis of 1-[2-deoxy-5-O-(4,4'-dimethoxytrityl)-β-D-erythro-pentofuranosyl]-N$^6$-dimethylaminomethylene-N$^2$,N3-etheno-adenosine-3'-[(2-cyanoethyl)-N,N-diisopropylphosphoramidite (Compound 29)

As depicted in Scheme 8, step c, to a solution of 5'-O-di-(4,4'-dimethoxy)trityl-N$^6$-dimethylaminomethylene-N$^2$, N3-etheno-2'-deoxy-adenosine, 28 (38 mg, 0.0587 mmol) in CH$_2$Cl$_2$ (0.5 ml) (iPr)$_2$EtN (20.46 μl, 2 eq) and 2-cyanoethyl diisopropyl-phosphoramido chloride (15.71 μl, 1.2 eq) were added and stirred for 5.5 h at room temperature under argon atmosphere. The mixture was diluted with CH$_2$Cl$_2$ (20 ml) and 5% aqueous NaHCO$_3$ and extracted with CH$_2$Cl$_2$ (3×15 ml). The combined organic layers were dried over Na$_2$SO$_4$ and evaporated under high vacuum to dryness to give a yellow oil. Product 29 was obtained in ca. 50% yield (22.6 mg). Due to hydrolysis of the phosphoramidite reagent H-phosphonate product could be detected by $^{31}$P-NMR at 10 ppm. $^1$H-NMR (300 MHz, CDCl$_3$): 9.49 (s, 1H, amidine); 7.82 (s, 1H, H8), 7.55 (Abq, 1H, etheno), 7.41 (Abq, 1H, etheno), 7.29-6.81 (m, 9H, trityl), 6.47 (dd, 1H, H-1', J=6.6, 13.2 Hz ), 4.70 (m, 1H, H-3'), 4.23-4.07 (m, 3H, H-4', 5'), 2.75 (m, 1H, H-2'), 2.35 (m, 1H, H-2'), 3.79 (s, 3H, OMe), 3.76 (s, 3H, OMe), 3.29 (s, 3H, CH$_3$), 3.27 (s, 3H, CH$_3$), 1.28-1.08 (m, 14H, isopropyl) ppm. MS (m/z): 848 (MH$^+$).

This phosphoramidite monomer can be used for synthesis of fluorescently-labeled oligonucleotides useful as probe for detection of DNA and RNA.

Example 16

Testing the Suitability of the Nucleoside Derivatives to the Automated DNA Synthesis Conditions In order for a compound to be used in automated DNA synthesis, it has to be able to withstand the conditions of the different reactions in the synthesis. For example, it has to be stable in the treatment with 28% ammonia for two hours at 60° C. The nucleoside 23 was tested in these conditions and was found to be stable according to TLC (8:2 CHCl$_3$: MeOH) and MS. It was tested also against 2% dichloroacetic acid used to remove the group DMT for 2 min, and it was found to be stable according to TLC (8:2 CHCl$_3$:MeOH) and MS.

Example 17

Biochemical Evaluation of the Novel Probes

The biochemical relevance of the new fluorescent analogues was evaluated with respect to several ATP-binding proteins. Therefore, nucleotide probes were evaluated either as ligands of the P2Y$_1$-receptor or substrates/inhibitors of Nucleoside Triphosphate Diphosphohydrolase, NTPDases1 and 2. For this purpose, the nucleotide analogues of 3, 4, 14a-c, and 16 have been prepared by a one-pot triphosphorylation reaction (Examples 5-11. compounds 30a-f).

To examine the efficacy of analogues 30a,d in a functional assay, we tested them by the agonist-induced Ca$^{2+}$ release in HEK 293 cells stably transfected with rat brain P2Y$_1$-receptor (FIG. 6) (Voehringer et al., 2000). Those P2Y$_1$-R-transfected cells were shown to be suitable for pharmacological characterization (Zuendorf et al., 2001). Analogue 30a, EC$_{50}$ in the range of 10$^{-7}$ M, was found to be almost equipotent with ATP. However, a benzyl substitution at N$^6$ of 30a, as in analogue 30d, reduced the ligand's potency. This resulted in a clear reduction by one order of magnitude for 30d. EC$_{50}$ value in the range of 10$^{-6}$ M.

For evaluation of the probes as substrates/inhibitors of NTPDase1 and 2, the analogues 30a-f were evaluated as either substrates or inhibitors of NTPDase1 and 2. We tested ATP and analogues 30 as substrates of NTPDases 1 and 2 at 100 μM for NTPDase1 and 200 μM for NTPDase2. All analogues were hydrolysed by NTPDases 1 and 2. NTPDase2 hydrolysed analogues 30 better than NTPDase1. When compared to ATP, the rate of hydrolysis of all analogues was lower for NTPDase1 and mostly similar for NTPDase2 (FIGS. 7A-7B). Analogue 30e was hydrolyzed less efficiently than ATP by both enzymes.

Next, we tested whether N$^2$,N3-ϵ-A is suitable for probing ectonucleotidases. Here, we demonstrated the superior fluorescent properties of N$^2$,N3-ϵ-A analogues as compared to ATP. Furthermore, the corresponding nucleotide N$^2$,N3-ϵ-A-TP, 30a, proved almost equipotent to ATP at the P2Y$_1$-R and NTPDase2. Next, we wanted to prove the suitability of our probes to various biochemical studies of these proteins, as monitored by fluorescence spectra. For this purpose, we measured the fluorescence spectra of 30a and its monophosphate homologue with and without human NTPDase2. We observed that the fluorescence intensity of the nucleotide decreased by ca. ⅓ upon the addition of the enzyme (not shown). This observation is consistent with the lower dielectric constant (polarity) of the protein as compared to that of the aqueous solution. Fluorescence intensity of the bound nucleotide, although lowered, still enables the application of this nucleotide as a fluorescent probe. Maximum emission (lambda max) for the free nucleotide does not shift upon the addition of the enzyme, implying that the catalytic site does not provide acidic environment (Tables 1-2).

For the fluorescence studies of 30a-NTPDase2 complex, emission spectra of 30a and its monophosphate homologue, 30a', were measured in the presence of human NTPDase2 using an Aminco-Bowman series 2 Luminescence Spectrometer. Measurement conditions included: 740-780 V sensitivity, 37° C. and excitation at 290 nm. The concentration of the samples was of the order of 2×10$^{-4}$ M in the NTPDase incubation mixture. Measurements of the emission spectra were performed in 1.5 ml of 200 μM 30a and 30a', without enzyme. Enzyme was added (3.6 μg of transfected COS-7 cells lysate), then, emission spectra were measured at 5 min intervals. Samples of reaction mixture (200 μl) were taken before each emission measurement and added to 50 μl of Malachite green reagent to estimate Pi released (see NTPDases activity assay).

CONCLUSIONS

We developed three short, facile, and regiospecific syntheses of $N^2,N3-\epsilon$-A, 4, starting from 2-amino-6-chloropurine riboside, 6, or 2-amino-6-thiomethyl-purine riboside, 16. Our synthetic procedures proved efficient not only for the formation of the novel angular analogue $N^2,N3-\epsilon$-A, 4, but also for the known $N^2,N3-\epsilon$-G, 3. Thus, in earlier syntheses, $N^2,N3-\epsilon$-G was achieved in a 25-48% yield (Kusmierek et al., 2000; Khazanchi et al., 1993), whereas in our procedure (Scheme 1), this compound was obtained in an 86% yield. The most convenient synthetic pathway for the preparation of 4 is a 3-step synthesis starting from thioguanosine 15 (Scheme 4).

The related analogue, $N^2,N3-\epsilon$-6-methylthiopurine riboside, 17, exhibits remarkable fluorescence ($\lambda_{max}$ 518 nm in water, $\phi$0.13).

$N^2,N3-\epsilon$-A-TP, 30a, proved to be almost equipotent to ATP at the $P2Y_1$-R and NTPDase2. Namely, the extension at the ATP's C2, N3-positions is tolerated by both proteins. Apparently, the major interactions of these proteins with the adenine moiety are at $N^1$,N6-positions, probably via H-bonds. The importance of H-bonding interactions of N6-amine with the protein binding-pocket are demonstrated by the significant reduction of the affinities of P2Y1-R and NTPDase2 to 30d and 30e, respectively.

Furthermore, analogue 30a proved fluorescent also in the protein-bound state, though with lower fluorescence intensity as compared to the free probe.

Based on the unique fluorescent and H-bonding properties, we propose the novel adenosines 4 and 23 and the ATP analogues 26 and 30a as useful probes for various biochemical applications.

APPENDIX A

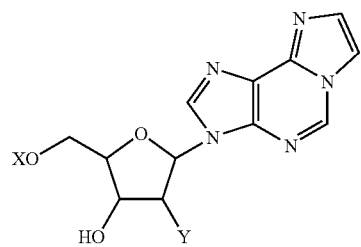

X = H, $PO_3^{2-}$; $P_2O_7^{3-}$; $P_3O_9^{4-}$
Y = OH, H

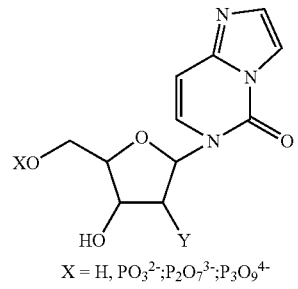

X = H, $PO_3^{2-}$; $P_2O_7^{3-}$; $P_3O_9^{4-}$
Y = OH, H

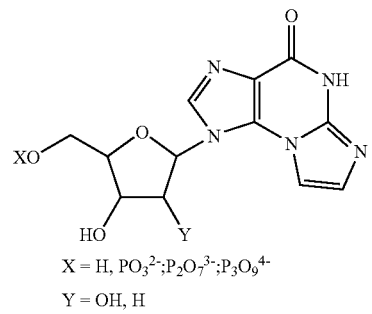

X = H, $PO_3^{2-}$; $P_2O_7^{3-}$; $P_3O_9^{4-}$
Y = OH, H

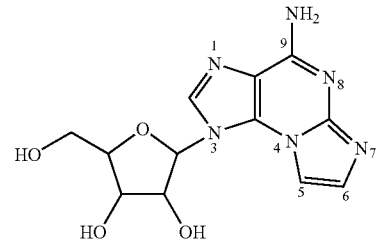

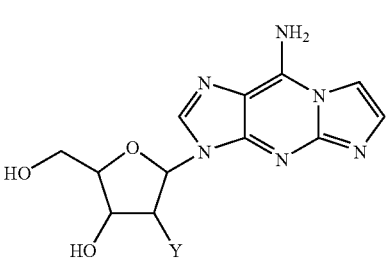

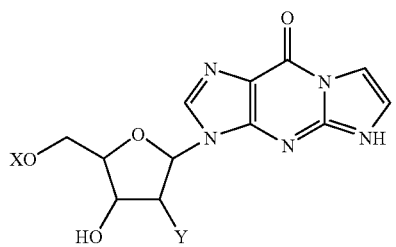

X = H, $PO_3^{2-}$; $P_2O_7^{3-}$; $P_3O_9^{4-}$
Y = OH, H

Scheme 1
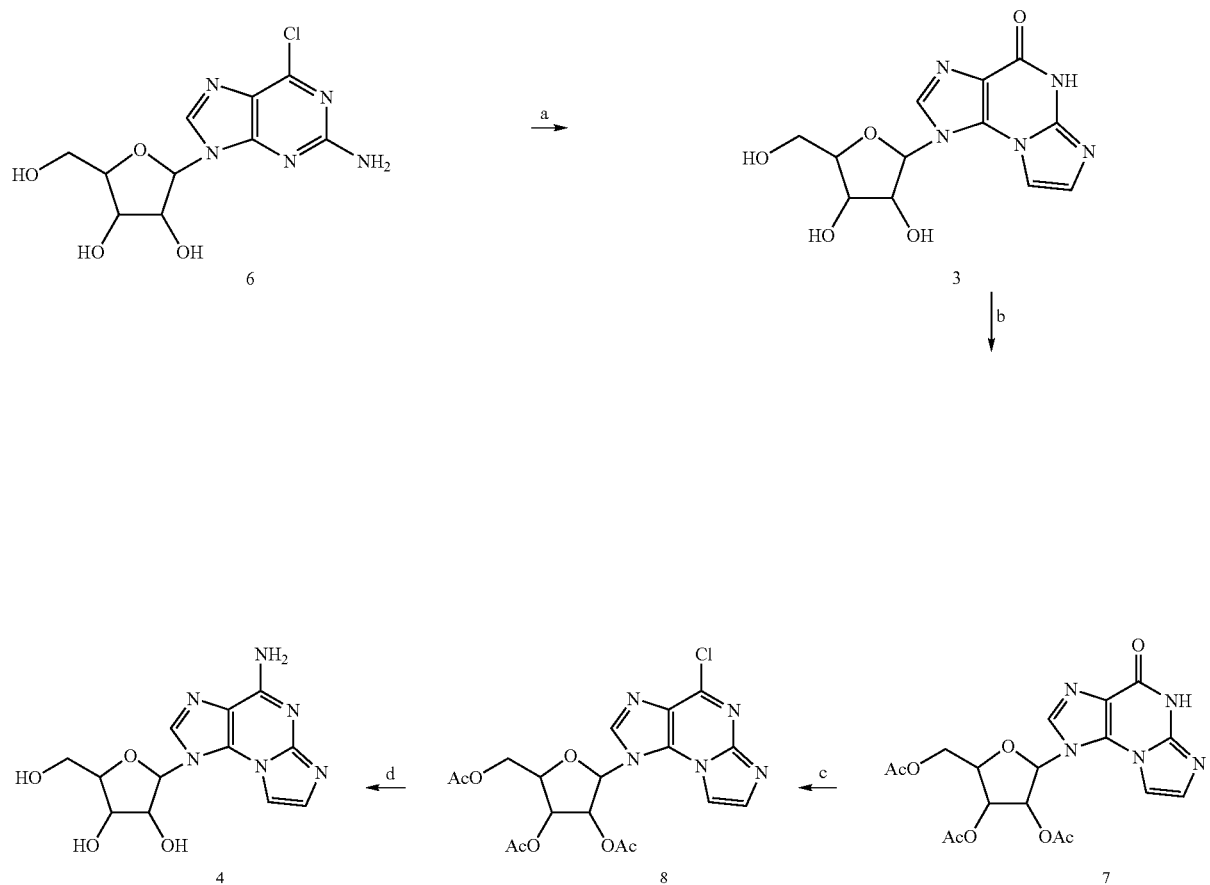
Reagents and conditions: (a) BrCH₂CHO, EtOH, buffer (pH 4.5), 38° C., 30 h (86%); (b) Ac₂O/Py, rt, 48 h (63%); (c) POCl₃, N,N-dimethylaniline, CH₃CN, 70° C., 1 h (56%); (d) 2 M NH₃/EtOH, 100° C., (43%)
-continued
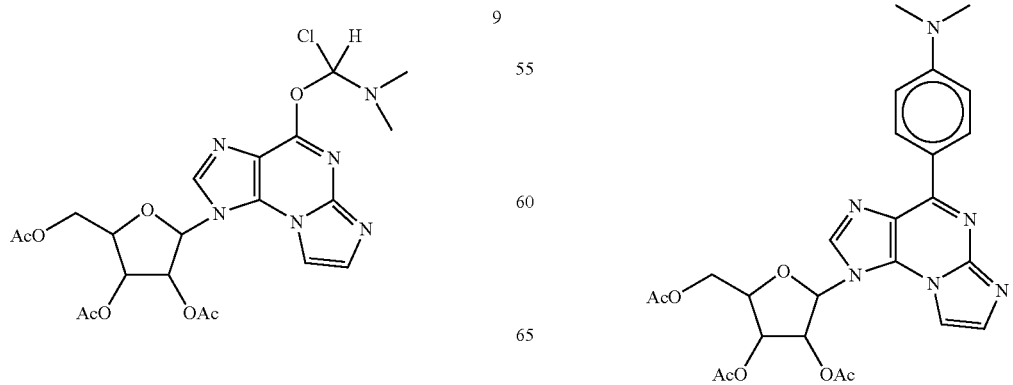

Scheme 2
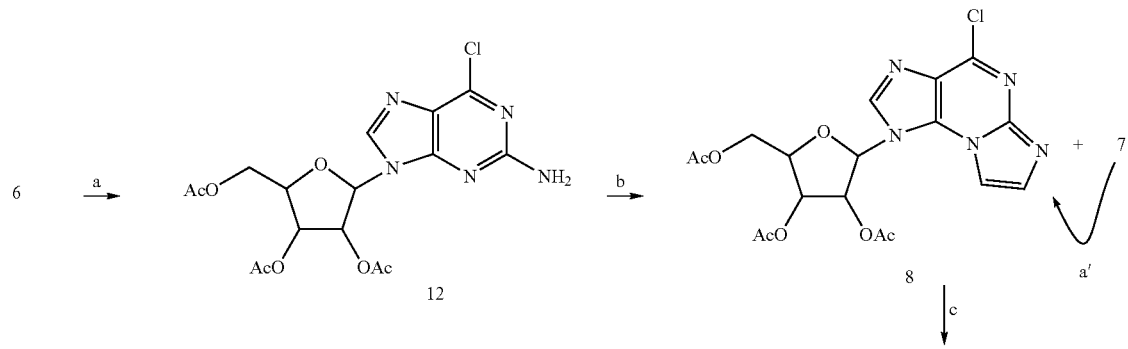
Scheme 2 - Reagents and conditions: (a) Ac₂O/Py, rt, 48 h (68%); (a′) POCL₃, N,N-dimethylaniline, CH₃CN, 70° C., 1 h (49%); (b) BrCH₂CHO, CHCl₃/EtOH, buffer (pH 4.5), 38° C., 30 h (38% 8 = 8% 7); (c) 2 M NH₃/EtOH, 100° C., 24 H (43%)
Scheme 3
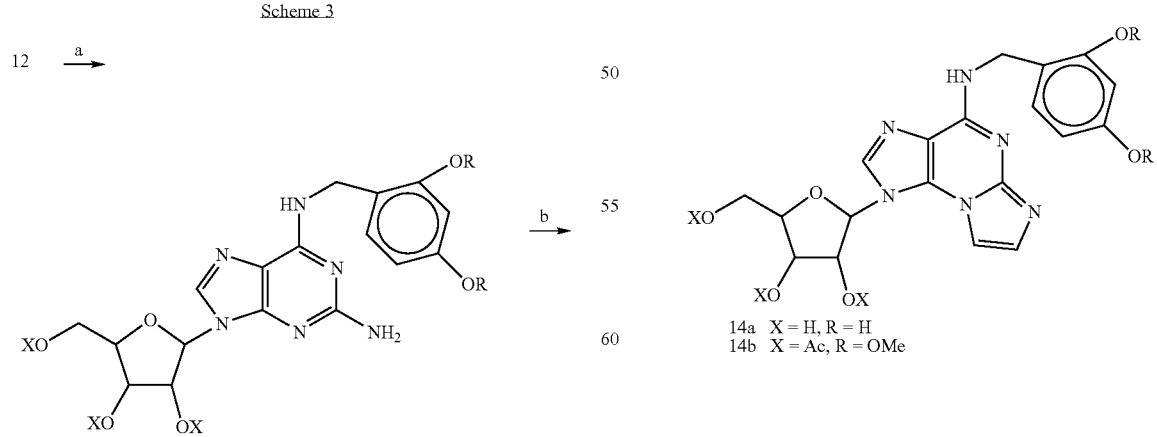
13a X = H, R = H
13b X = Ac, R = OMe
14a X = H, R = H
14b X = Ac, R = OMe
Scheme 3 - Reagents and conditions: (a) 2,4-di-Ome-benzylamine, EtOH, 60° C., 36 h (91%); (b) BrCH₂CHO, CHCl₃/EtOH, buffer (pH 4.5), 38° C., 30 h (73%)

Scheme 4
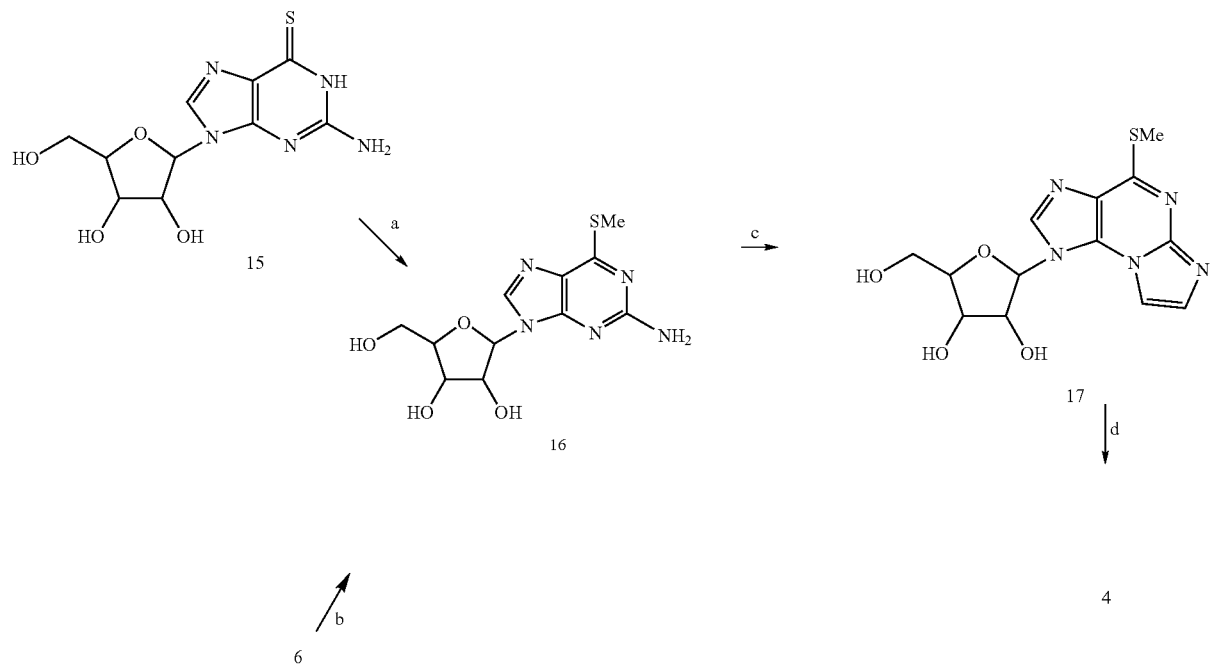
Scheme 4 - Reagents and conditions: (a) NaOH (aq), MeI (84%);
(b) NaSMe, DMSO, 60° C., 40 h (26%); (C) BrCH$_2$CHO,
CHCl$_3$/EtOH, buffer (Ph 4.5), 38° C., 30 h (33%); (d) 2M NH$_3$/EtOH,
150° C., 6 h (33%)
Scheme 5
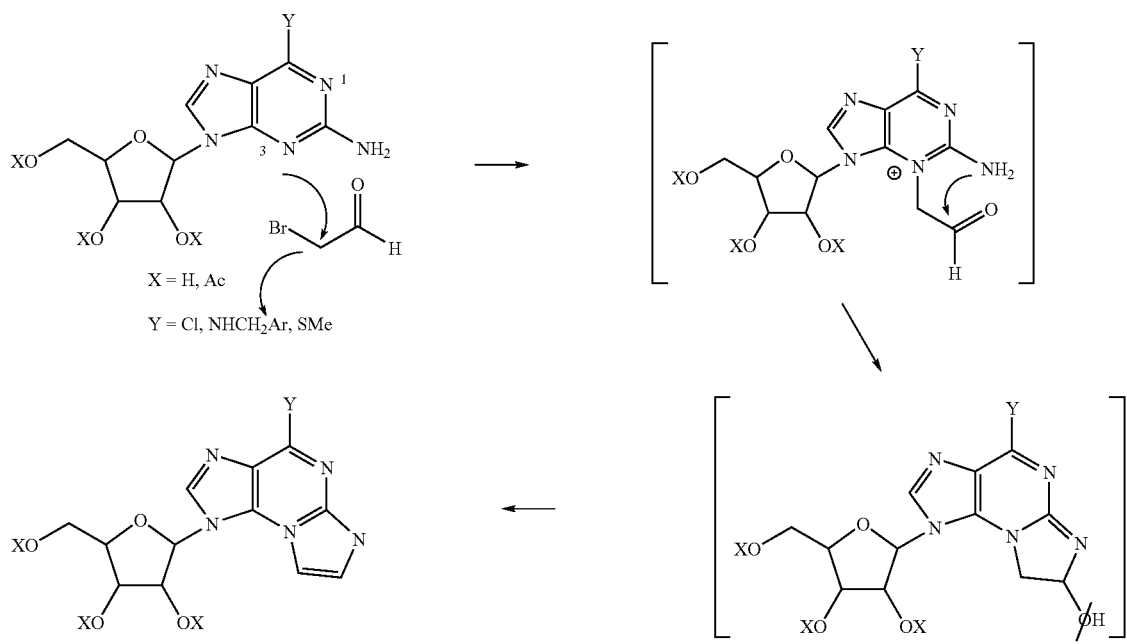
X = H, Ac
Y = Cl, NHCH$_2$Ar, SMe

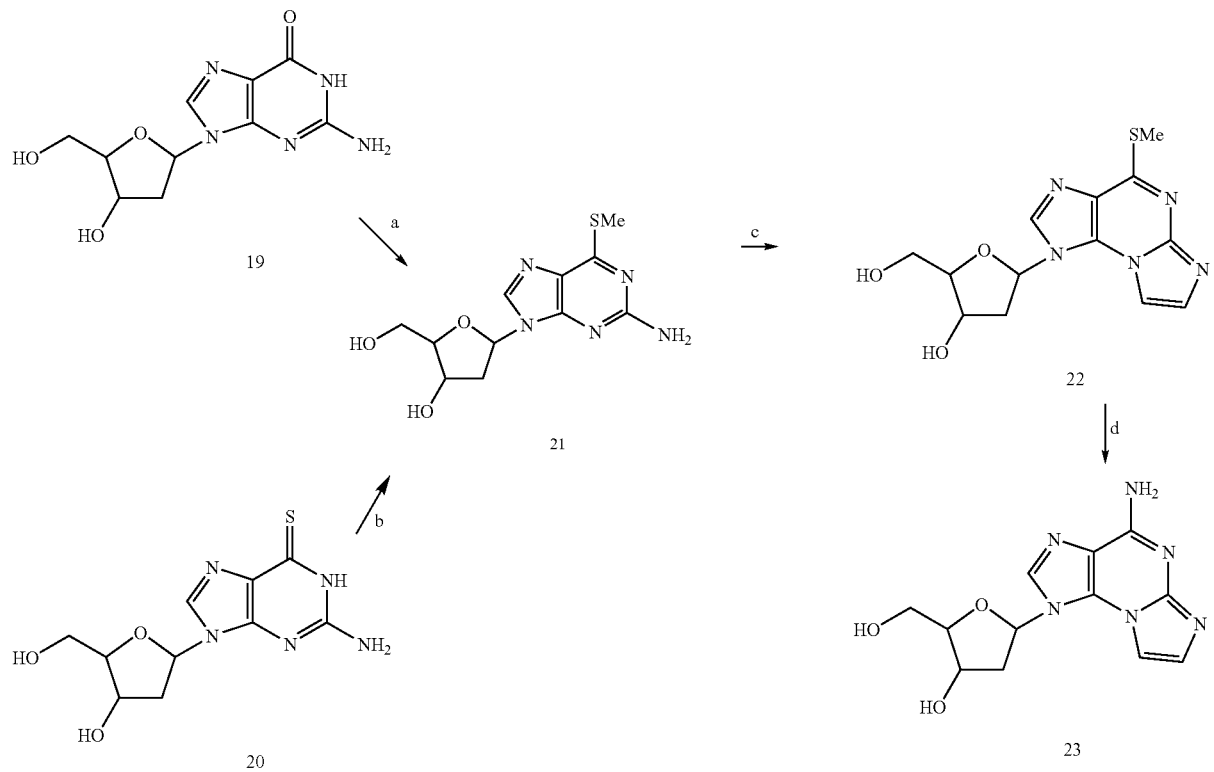
Scheme 6
Reagents and conditions: (a) TFAA, NaSCH₃, Py, 24 h;
(b) MeI, 0.4 M NaOH, 2 h; (c) 1.3 M BrCH₂C(O)H, 1 M
NH₄NCO₃/10% HCl, 8 h; (d) 2.0 M NH₃/EtOH, 100° C., 24
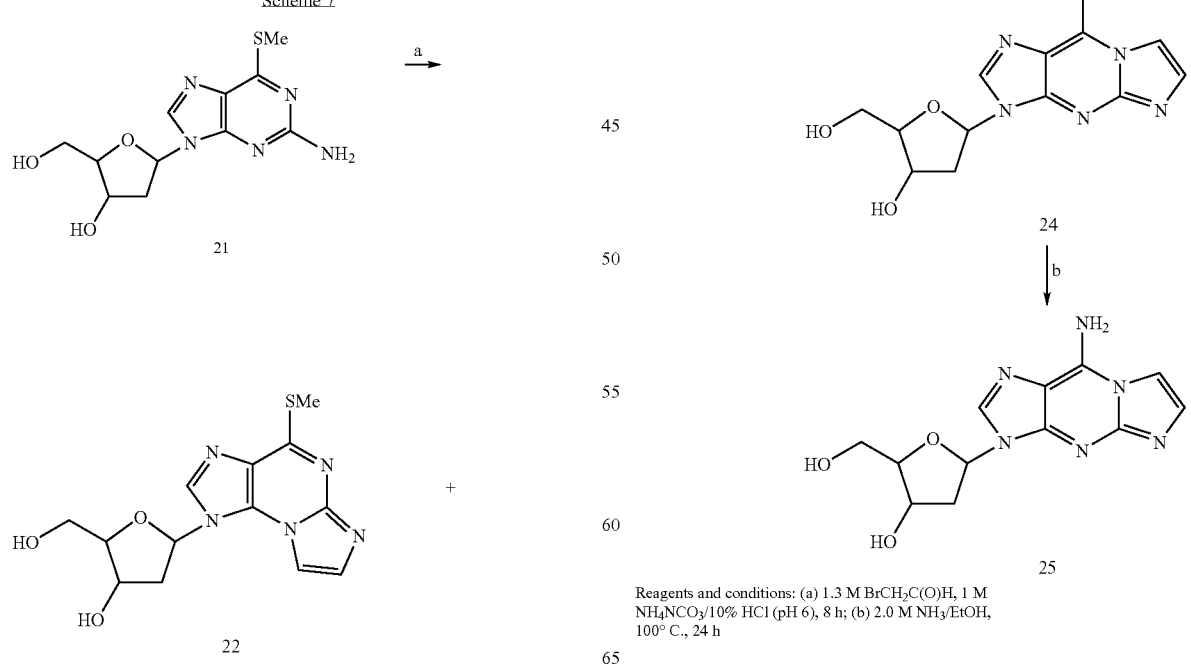
Reagents and conditions: (a) 1.3 M BrCH₂C(O)H, 1 M
NH₄NCO₃/10% HCl (pH 6), 8 h; (b) 2.0 M NH₃/EtOH,
100° C., 24 h Scheme 8

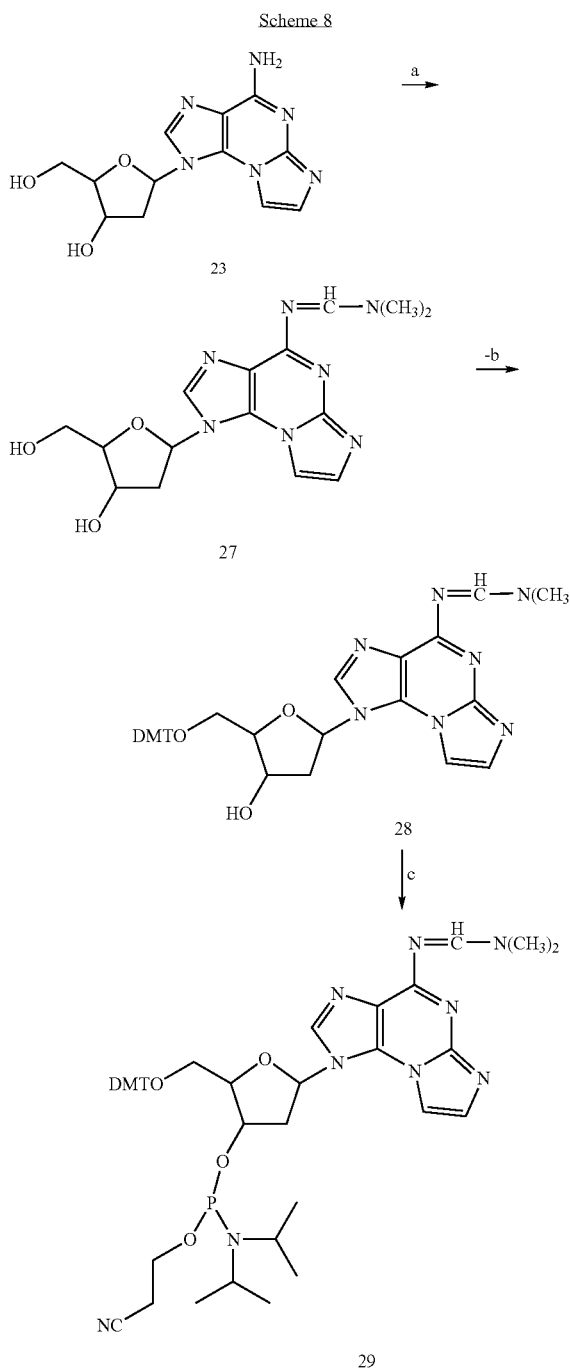

Reagents and conditions: (a) Dimethylformamide dimethylacetal, DMF, 80° C., 24 h; (B) 4,4'–dimethoxytrityl chloride, Py, 48 h; (c) Bis(diisopropylamino-β-cyanoethoxyphosphine, ethyldiisopropylamine, $CH_2Cl_2$, 5.5 h

REFERENCES

Andrew, T. C. Tsin, G. T. Hugo, A., *Life Sciences*, 1988, 43, 1379-1384

Beland, F. A. Fullerton, N. F. Heflich, R. H., Rapid isolation, hydrolysis and chromatography of formaldehyde-modified DNA, *J. Chromatogr.* 1984, 308, 121-131

Boryski, J., 1,N2-ethenoguanosine: Three methods of synthesis. Nucleosides, *Nucleotides,* 1990, 9, 803-813

Callis, P. R., *Ann. Rev. Phys. Chem.,* 1983, 34, 329-357

Campbell, J. B. Greene, J. H. Lavagnino, E. R. Gardner, D. N. Pike, A. J., Some new methods for preparing 2,3- and 3,4- diaminopyridines, *J. Heterocyclic. Chem.,* 1986, 23, 669-672

Cheng, K. C. Preston, B. D. Cahill, D. S. Dosanjh, M. K. Singer, B. Loeb, L. A., The vinyl chloride DNA derivative N2,3-ethenoguanine produces G→A transitions in *Escherichia coli, Proc Natl Acad Sci U.S.A.,* 1991, 88, 9974-9978

Chi, Huguyen, Emile, B., A general route to 5-and 6-substituted 4-amino-2-oxo-1,2-dihydropyridines, *Synthesis. Communications,* 1984, 765-766

Eritja, R. Kaplan. B. E. Mhaskar, D. Sowers, L. C. Petruska, J. Goodman, M. F., Synthesis and properties of defined DNA oligomers containing base mispairs involving 2-aminopurine, *Nucleic Acids Res.,* 1986, 14, 5869-5884

Fischer, B. Boyer, J. L. Hoyle, C. H. V. Ziganshim, A. U. Brizzolara, A. L. Knight, G. E. Zimmet, J. Burnstock, G. Harden, T. K. Jacobson, K. A., *J. Med. Chem.* 1993, 36, 3937-3946

Glemarec, C. Besidsky, Y. Chattopadhyaya, J. Kusmierek, J. Lahti, M. Oivanen, M. Lonnberg, H., N2,3-ethenoguanosine and ia'-metamorphosine: Nitrogen-15 NMR spectroscopy and elucidation of physicochemical properties by kinetic and equilibrium measurements, *Tetrahedron,* 1991, 47, 6689-6704

Guillermo, G. N. Angeles, B. Nuria, R. Teresa, G. Rosario, G. M., Amino acid-derived 4-alkyl-4-carboxy-2-azetidinones. New insights into b-lactam ring formation and N-deprotection, *Heterocycles,* 2002, 56, 501-514

Hand, E. S. Paudler, W. W., Mechanism of the reaction of 2-haloketones with 2-aminopyridine, *Tetrahedron,* 1982, 38, 49-55

Haugland, R. P., Handbook of fluorescent probes and research products, *Molecular Probes,* 2002

Jack, J. W. Alexander, H. Iris, L., Thiation of nucleoside. I. synthesis of 2-amino-6-mercapto-9- -D-ribofuranosylpurine ("thioguanosine") and related purine nucleosides, *J. Am Chem. Soc.,* 1958, 80, 1669-1675

Mandal, A. K. Shrotri, P. Y. Ghogare, A. D., Boron trifluoride etherate/iodide ion, a novel reagent for the non-aqueous conversion of acetals to carbonyl compounds, *Synthesis,* 1986, 11, 221-222

Khazanchi, R. Yu, P. L. Johnson, F., N2,3-etheno-2'-deoxyguanosine[8,9-dihydro-9-oxo-2'-deoxy-3-b-d-ribo-furanosylimidazo[2,1-b]purine]: a practical synthesis and characterization, *Journal of Organic Chemistry,* 1993, 58, 2552-2556

Kikugawa, K. Kawashima, T., Vilsmeier-Haack reaction. Characterization of thionyl chloride-dimethyl formamide complexes, *Chem. Pharm. Bull.,* 1971, 19, 2629-2630

Kochetkov, N. K. Shibaev, V. N. Kost, A. A., *Tetrahedron Letters* (1971), 21, 1993

Kung, P. Jones, R. A., *Tetrahedron Lett.,* 1991, 32, 3919-3922

Kusmierek, J. T. Folkman, W. Singer, B., Synthesis of N2,3-ethenodeoxyguanosine, N2,3-ethenodeoxyguanosine 5'-phosphate, and N2,3-ethenodeoxyguanosine 5'-triphosphate. Stability of the glycosyl bond in the monomer and in poly (dG, epsilon dG-dC), *Chem Res Toxicol.,* 1989, 2, 230-233

Kusmierek, J. T.; Jensen, D. E. Spengler, S. J. Stolarski, R. Singer, B., Synthesis and properties of N2,3-ethenoguanosine and N2,3-ethenoguanosine 5'-diphosphate, *J. Org. Chem.,* 1987, 52, 2374-2378

Kusmierek, J. T. Singer, B., 1,N2-ethenodeoxyguanosine: Properties and formation in chloroacetaldehyde-treated polynucleotides and DNA, *Chem Res Toxicol.*, 1992, 5, 634-638

Leonard, N. J., *Biochem. Mol. Biol.*, 1992, 3, 273-297

Leonard, N. J., Etheno-substituted nucleotides and coenzymes: fluorescence and biological activity, CRC *Crit. Rev Biochem.*, 1984, 15, 125-199

Major, D. T. Laxer, A. Fischer, B., Protonation studies of modified adenine and adenine nucleotides by theoretical calculations and (15)N NMR, *J Org Chem.*, 2002, 67, 790-802

Michael, J. Jean, M.: Exploring the 2,2'-diamino-5,5'-bipyrimidine hydrogen-bonding motif: a modular approach to alkoxy-functionalized hydrogen-bonded networks, *Helv. Chim. Acta*, 1998, 81, 1921-1930

Sattsangi, P. D. Leonard, N. J. Frihart, C. R., 1,N2-ethenoguanine and N2,3-ethenoguanine. Synthesis and comparison of the electronic spectral properties of these linear and angular triheterocycles related to the Y bases, *J Org Chem.*, 1977, 42, 3292-3296

Secrist, J. A. Bario, J. R. Leonard, N. J. Weber, G., *Biochemistry*, 1972, 11, 3499-3506

Secrist, J. A. Shortnacy-fowler, A. Bennett, L. Montgomery, J. A., Synthesis and biological evaluation of 8-substituted derivatives of nebularine (9-b-D-ribofuranosyl-purine), *Nucleosides & Nucleotides*, 1994, 13, 1017-1029

Simon, R. Vinod, K., Synthesis of 6-15N-and 1-15N-labeled adenosine monophosphates, *Tetrahedron*, 1988, 44, 6367-6372

Thomas, R. W. Leonard, N. J., *Heterocycles*, 1976, 5, 839-882

Veliz, E. A. Beal, P. A, C6 substitution of inosine using hexamethyl-phosphorous triamide in conjunction with carbon tetrahalide or N-halosuccinimide, *Tetrahedron Letters*, 2000, 41, 1695-1697

The invention claimed is:

1. A compound of the formula I and an oligonucleotide comprising one or more moieties thereof, said compound having the formula:

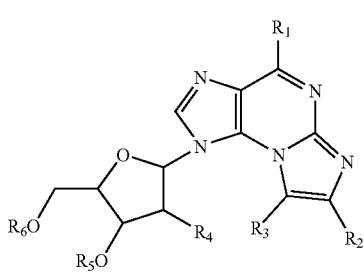

I wherein
$R_1$ is —$NHR_7$, halo, —$SR_7$ or —N═CH—N(CH$_3$)$_2$;
$R_2$ and $R_3$, the same or different, each is H, hydrocarbyl, —$NR_7R_8$, —$SR_7$ or —$OR_7$;
$R_4$ is H or —$OR_9$;
$R_5$, $R_6$ and $R_9$ the same or different each is H, alkanoyl, $PO_3^{2-}$, $P_2O_6^{3-}$, $P_3O_9^{4-}$; or $R_5$ is 2-cyanoethyl-N,N-diisopropyl-phosphoramidite and $R_6$ is 4,4'-dimethoxytrityl;

$R_7$ and $R_8$ the same or different each is H, hydrocarbyl or heterocyclyl;
and salts thereof.

2. A compound according to claim 1, wherein $R_1$ is NH$_2$, $R_4$ is OH, and $R_2$, $R_3$, $R_5$ and $R_6$ each is H (compound 4).

3. A compound according to claim 1, wherein $R_1$ is NH$_2$, and $R_2$, $R_3$, $R_4$, $R_5$ and $R_6$ each is H (compound 23).

4. A compound according to claim 1, wherein $R_1$ is —$NHR_7$ and $R_7$ is H or a hydrocarbyl radical selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_6$-$C_{10}$ aryl and ($C_6$-$C_{10}$)aryl-($C_1$-$C_8$)alkyl and the aryl may be unsubstituted or substituted by one or more OH, $C_1$-$C_4$ alkyl, —O—($C_1$-$C_4$)alkyl, or —S—($C_1$-$C_4$)alkyl groups.

5. A compound according to claim 1, wherein $R_1$ is —$SR_7$ and $R_7$ is hydrocarbyl selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_6$-$C_{10}$ aryl and ($C_6$-$C_{10}$)aryl-($C_1$-$C_8$)alkyl and the aryl may be unsubstituted or substituted by one or more OH, $C_1$-$C_4$ alkyl, —O—($C_1$-$C_4$)alkyl, or —S—($C_1$-$C_4$)alkyl groups.

6. A compound according to claim 1, wherein $R_1$ is —NHR, R is 2,4-dimethoxybenzyl, $R_2$ and $R_3$ each is H, $R_4$ is —$OR_7$, and $R_5$, $R_6$ and $R_7$ each is acetyl (compound 14b).

7. A compound according to claim 1, wherein $R_1$ is —Smethyl, $R_2$ and $R_3$ each is H, $R_4$ is —OH, and $R_5$ and $R_6$ each is H (compound 17).

8. A compounds according to claim 1, wherein $R_1$ is —Smethyl, and $R_2$, $R_3$, $R_4$, $R_5$ and $R_6$ each is H (compound 22).

9. A compound according to claim 1, wherein $R_1$ is —NH$_2$, and $R_2$, $R_3$, $R_4$ and $R_5$ each is H, and $R_6$ is $P_3O_9^{4-}$ (compound 26).

10. A compound according to claim 1, wherein $R_1$ is —NH$_2$, $R_4$ is OH, $R_2$, $R_3$, and $R_5$ each is H, and $R_6$ is $P_3O_9^{4-}$ (compound 30a).

11. A compound according to claim 1, wherein $R_1$ is —N═CH—N(CH$_3$)$_2$; $R_2$, $R_3$, and $R_4$, each is H; $R_6$ is 4,4'-dimethoxytrityl, and $R_5$ is 2-cyanoethyl-N,N-diisopropyl-phosphoramidite (compound 29).

12. A DNA or RNA oligonucleotide according to claim 1, comprising one or more moieties of a fluorescent compound of formula I.

13. An oligonucleotide according to claim 12, wherein the moiety is attached to the 3'- and/or 5'-terminus of the oligonucleotide sequence.

14. An oligonucleotide according to claim 12, wherein the moiety is incorporated into the oligonucleotide by a chemical synthesis via the phosphoramidite synthesis.

15. A fluorescent 3'- or 5'-labeled probe composed of an oligonucleotide of claim 12.

16. A process for the preparation of N$^2$,N3-etheno-guanosine (compound 3), which comprises reacting 6-chloro-2-amino-purine-riboside (compound 6) with bromoacetaldehyde.

17. A method for detection and quantitation of DNA or RNA in genetic material using a labeled probe wherein said labeled probe is a fluorescent compound or a fluorescent oligonucleotide probe defined in claim 1.

* * * * *